United States Patent [19]

Rody et al.

[11] Patent Number: 4,933,271
[45] Date of Patent: Jun. 12, 1990

[54] STABILIZERS FOR COLOR PHOTOGRAPHY RECORDING MATERIALS

[75] Inventors: Jean Rody, Riehen; David G. Leppard, Marley, both of Switzerland

[73] Assignee: Ciba-Geigy AG, Basel, Switzerland

[21] Appl. No.: 251,081

[22] Filed: Sep. 29, 1988

[30] Foreign Application Priority Data

Sep. 30, 1987 [CH] Switzerland ............... 3799/87

[51] Int. Cl.⁵ .................................. G03C 7/32
[52] U.S. Cl. ..................... 430/512; 430/551; 430/372; 430/931
[58] Field of Search ............ 430/512, 551, 931, 372, 430/611, 546

[56] References Cited

U.S. PATENT DOCUMENTS

| | | | |
|---|---|---|---|
| 3,253,921 | 5/1966 | Sawdey | 96/73 |
| 3,533,794 | 10/1970 | Ohi et al. | 96/84 |
| 3,935,016 | 1/1976 | Nishimura et al. | 96/74 |
| 4,228,235 | 10/1980 | Okonogi et al. | 430/542 |
| 4,452,884 | 6/1974 | Leppard | 430/551 |
| 4,465,765 | 8/1984 | Leppard et al. | 430/512 |
| 4,526,864 | 7/1985 | Takada et al. | 430/551 |
| 4,558,131 | 12/1985 | Leppard et al. | 546/222 |

*Primary Examiner*—Richard L. Schilling
*Attorney, Agent, or Firm*—Wenderoth, Lind & Ponack

[57] ABSTRACT

Tetrahydrothiopyran compound of the formula I

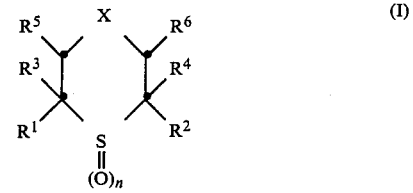

in which $R^1$, $R^2$, $R^3$, $R^4$, $R^5$, $R^6$, X and n are as defined in claim 1, are effective stabilizers for dyes and dye couplers in photographic layers. In particular, they provide protection from damage by light. They are preferably used in combination with a phenolic antioxidant.

12 Claims, No Drawings

STABILIZERS FOR COLOR PHOTOGRAPHY RECORDING MATERIALS

The present invention relates to photostabilization of photographic dyes and dye couplers by addition of a stabilizer into the photographic layer. The addition can be in the yellow layer, magenta layer or cyan layer. The effect can be increased further by addition of a phenolic antioxidant.

Most of the current customary silver colour picture processes are based on a chemical reaction between a dye coupler—a compound with a reactive methylene or pseudomethylene group—and an oxidized developer. The developer—usually a p-phenylenediamine derivative—is thereby oxidized by the photosensitized silver halide to form metallic silver. The oxidized developer is the actual reagent for dye formation.

Depending on their chemical structures, the colour couplers require either 2 or 4 mol of silver per mol of coupler. Diequivalent or tetraequivalent couplers are therefore referred to.

Colour photography materials based on such a process have at least three colour-sensitive layers which contain three different types of couplers:

(a) The yellow layer containing a yellow coupler. These are usually β-ketocarboxamides.

(b) The cyan layer containing a cyan coupler. These are usually phenols or naphthols.

(c) The purple or magenta layer containing a magenta coupler. These are usually pyrazolones, pyrazoloazoles, cyanoacetylcoumarones or open-chain acylacetonitriles.

To avoid diffusion of the couplers into the adjacent layer, the compounds are provided with hydrophobic ballast groups or are bonded into polymeric structures.

The yellow dyes formed after development have an inadequate light-fastness. The light-fastness can be improved to a certain degree by introducing a layer containing a UV absorber above the yellow layer, as has been proposed, for example, in U.S. Pat. No. 3,253,921.

Another, better route is to add special stabilizers to the yellow layer. These must not react with the coupler or developer. Various phenolic compounds have been proposed as such stabilizers, but in particular p-hydroxybenzoic acid ester derivatives, such as have been proposed, for example, in U.S. Pat. No. 4,228,235, and combinations of sterically hindered amines with phenols, such as have been proposed, for example, in EP-A-144,029. Molecular combinations of hindered amines and phenolic groups have also been proposed, for example, in EP-A-82,817 and EP-A-103,540. Such stabilizers have led to a considerable increase in the light-fastness, but there is continued interest in improvements in the light-fastness of the yellow dyes.

The magenta dyes and couplers are also not sufficiently fast to light. There is also a thermal instability of many magenta couplers when stored in the dark. As with the yellow dyes, filter layers with UV absorbers, in particular with hydroxyphenylbenzotriazoles, have also been proposed for the magenta dyes and magenta couplers, for example in U.S. Pat. No. 3,533,794, but this is not sufficient for the current requirements of light-fastness.

The addition of stabilizers in the magenta layer is effective. Suitable stabilizers of this type are, in particular, hydroquinone derivatives, such as are described, for example, in U.S. Pat. No. 3,935,016.

The cyan dyes must also be stabilized. This can likewise be effected by UV absorber filter layers, or by addition of special stabilizers to the cyan layer. Such stabilizers can be, for example, phenols or hindered amines, as described in EP-A-113,124.

The present invention relates to a colour photography recording material containing in at least one layer, as a stabilizer, at least one tetrahydrothiopyran compound of the formula I

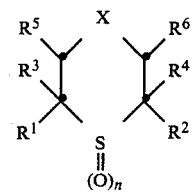

in which n is 0, 1 or 2, $R^1$ and $R^2$ independently of one another are hydrogen or methyl, $R^3$ and $R^4$ independently of one another are hydrogen, $C_1$–$C_4$alkyl, phenyl, thienyl or phenyl which is substituted by 1 or 2 $C_1$–$C_8$alkyl groups, cyclohexyl, phenyl, $C_7$–$C_9$phenylalkyl, $C_1$–$C_{18}$alkoxy or halogen, $R^5$ and $R^6$ independently of one another are hydrogen, $C_1$–$C_4$alkyl, phenyl, —COO($C_1$–$C_{18}$alkyl), —CO—$CH_3$, —CO—phenyl, —CH($OR^7$)—$CH_3$ or —CH($OR^7$)—phenyl and $R^7$ is hydrogen, $C_1$–$C_{12}$alkyl, $C_2$–$C_{18}$alkanoyl or benzoyl, X is a divalent radical which completes the ring of the formula I to form a tetrahydrothiopyran ring and consists of one of the following groups:

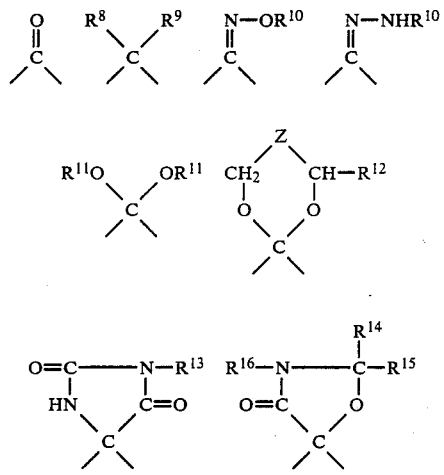

in which $R^8$ is hydrogen, methyl, phenyl, —CN, —$CONH_2$, —COO($C_1$–$C_4$alkyl) or —P(O)(O$C_1$–$C_4$alkyl)$_2$, $R^9$ is hydrogen, $OR^{17}$ or —N($R^{18}$)($R^{19}$), $R^{10}$ is hydrogen, $C_1$–$C_{18}$alkyl, $C_2$–$C_{18}$alkanoyl or benzoyl, $R^{11}$ is $C_1$–$C_{12}$alkyl, allyl or benzyl, $R^{12}$ is hydrogen, $C_1$–$C_4$alkyl or —$CH_2OR^{20}$, $R^{13}$ is hydrogen, $C_1$–$C_{18}$alkyl, $C_7$–$C_9$aralkyl, cyclohexyl or phenyl, $R^{14}$ and $R^{15}$ independently of one another are hydrogen, $C_1$–$C_{12}$alkyl or phenyl or $R^{14}$ and $R^{15}$ together are $C_4$–$C_{11}$alkylene, $R^{16}$ is hydrogen, $C_1$–$C_{12}$alkyl, —COO($C_1$–$C_4$alkyl)-substituted $C_1$–$C_4$alkyl, allyl or benzyl, $R^{17}$ is hydrogen, $C_1$–$C_{12}$alkyl, allyl, benzyl, $C_2$–$C_{18}$alkanoyl, benzoyl, a group —CO—O—$R^{27}$ or —CO—NH—$R^{27}$ or a group of the formula II or III

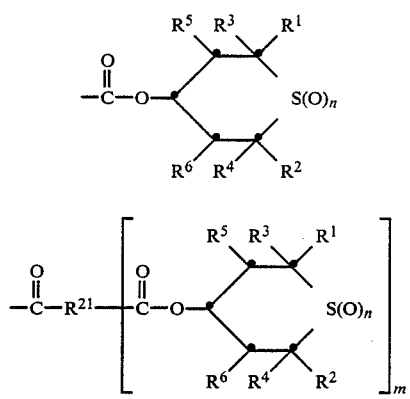  II

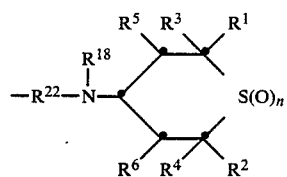  III in which m is 1, 2 or 3, $R^{18}$ is hydrogen, $C_1$–$C_{12}$alkyl, $C_2$–$C_{18}$alkanoyl, benzoyl, $C_1$–$C_{12}$alkoxycarbonyl, phenoxycarbonyl or phenylaminocarbonyl, $R^{19}$ is hydrogen, $C_1$–$C_{12}$alkyl, cyclohexyl, benzyl, phenyl or a group of the formula IV

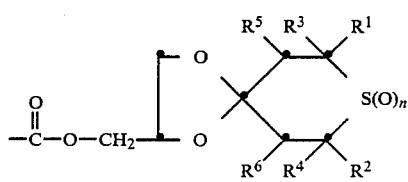  IV $R^{20}$ is hydrogen, $C_1$–$C_4$alkyl, $C_2$–$C_{18}$alkanoyl, benzoyl or a group of the formula V or VI

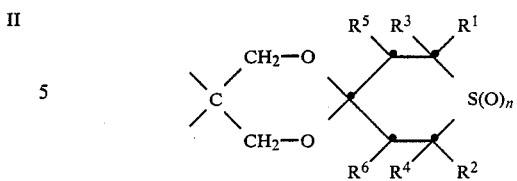  V

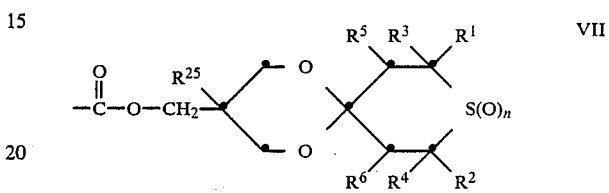  VI in which m is 1, 2 or 3, $R^{21}$, if m is 1, is a direct bond, $C_1$–$C_{12}$alkylene, $C_2$–$C_6$alkylene which is substituted by phenyl or benzyl or interrupted by —O— or —S—, vinylene, phenylene or a group —NH—$R^{28}$—NH—, and if m is 2, is $C_3$–$C_{12}$alkanetriyl or $C_6$–$C_{12}$arenetriyl, and if m is 3, is $C_4$–$C_{12}$alkanetetrayl or $C_6$–$C_{12}$arenetetrayl, $R^{22}$ is $C_2$–$C_{12}$alkylene, $C_4$–$C_8$alkenylene, xylylene or a group —CO—$R^{23}$—CO—, in which $R^{23}$ is $C_1$–$C_{12}$alkylene which is substituted by phenyl or benzyl or interrupted by —O— or —S—, vinylene or phenylene, Z is a direct bond, a group

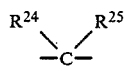

or a group of the formula

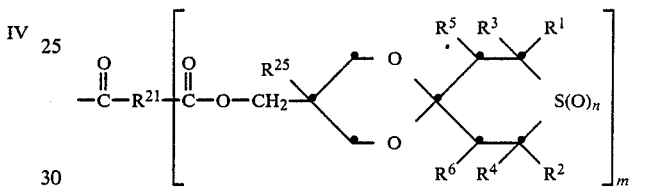

in which $R^{24}$ is hydrogen, $C_1$–$C_4$alkyl, —OH or —CH$_2$O$R^{26}$, $R^{25}$ is hydrogen or $C_1$–$C_4$alkyl and $R^{26}$ is hydrogen, $C_1$–$C_4$alkyl, $C_2$–$C_{18}$alkanoyl, benzoyl or a group of the formula VII or VIII

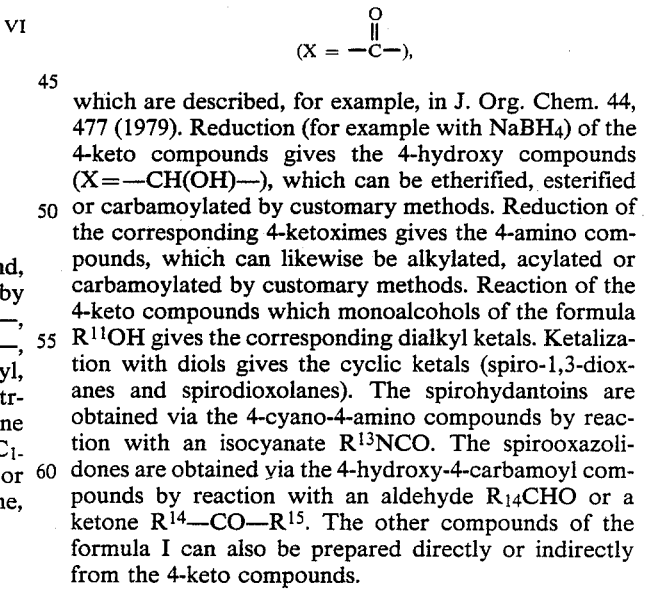

in which m is 1, 2 or 3, $R^{27}$ is $C_1$–$C_{12}$alkyl or phenyl and $R^{28}$ is $C_1$–$C_{12}$alkylene, $C_6$–$C_{12}$cycloalkylene, phenylene, naphthylene or phenylene which is substituted by $C_1$–$C_4$alkyl, $C_1$–$C_4$alkoxy or halogen.

If one of the substituents is alkyl, alkylene or alkanoyl, this radical may be unbranched or branched.

The compounds of the formula I are in some cases known compounds, in particular the 4-keto compounds $$(X = -\overset{\overset{\displaystyle O}{\|}}{C}-),$$

which are described, for example, in J. Org. Chem. 44, 477 (1979). Reduction (for example with NaBH$_4$) of the 4-keto compounds gives the 4-hydroxy compounds (X=—CH(OH)—), which can be etherified, esterified or carbamoylated by customary methods. Reduction of the corresponding 4-ketoximes gives the 4-amino compounds, which can likewise be alkylated, acylated or carbamoylated by customary methods. Reaction of the 4-keto compounds which monoalcohols of the formula $R^{11}$OH gives the corresponding dialkyl ketals. Ketalization with diols gives the cyclic ketals (spiro-1,3-dioxanes and spirodioxolanes). The spirohydantoins are obtained via the 4-cyano-4-amino compounds by reaction with an isocyanate $R^{13}$NCO. The spirooxazolidones are obtained via the 4-hydroxy-4-carbamoyl compounds by reaction with an aldehyde $R_{14}$CHO or a ketone $R^{14}$—CO—$R^{15}$. The other compounds of the formula I can also be prepared directly or indirectly from the 4-keto compounds.

The colour photography recording material preferably contains a compound of the formula I in which n is 0 or 2, $R^1$ and $R^2$ are hydrogen or methyl, $R^2$ and $R^3$ are methyl, phenyl, thienyl or phenyl which is substituted by 1 or 2 $C_1$–$C_4$alkyl groups, by cyclohexyl, $C_1$–$C_4$alkoxy or chlorine, $R^5$ and $R^6$ independently of one another are hydrogen, methyl, acetyl or benzoyl, X is one of the following groups:

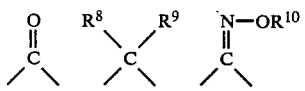

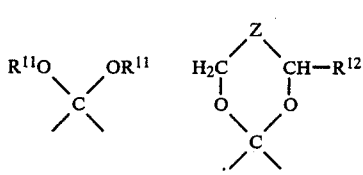

in which $R^8$ is hydrogen, methyl, phenyl or —P(O)(OC$_1$–C$_4$alkyl)$_2$, $R^9$ is hydrogen, —OR$^{17}$ or —NHR$^{18}$, $R^{10}$ is hydrogen or $C_2$–$C_{18}$alkanoyl, $R^{11}$ is $C_1$–$C_4$alkyl, $R^{12}$ is hydrogen, $C_1$–$C_4$alkyl or —CH$_2$OR$^{20}$, Z is a direct bond or a group —C(R$^{24}$)(R$^{25}$)—, $R^{17}$ is hydrogen, $C_2$–$C_{18}$alkanoyl, benzoyl or a group of the formula III in which m is 1 and $R^{21}$ is $C_1$–$C_{12}$alkylene, vinylene or phenylene, $R^{18}$ is $C_2$–$C_{12}$alkanoyl or benzoyl, $R^{20}$ is hydrogen, $C_2$–$C_{12}$alkanoyl, benzoyl or a group of the formula VI in which m is 1, $R^{24}$ is hydrogen, $C_1$–$C_4$alkyl or —CH$_2$OR$^{26}$, $R^{25}$ is hydrogen or $C_1$–$C_4$alkyl and $R^{26}$ is hydrogen, $C_2$–$C_{12}$alkanoyl, benzoyl or a group of the formula VIII in which m is 1.

The recording material particularly preferably contains a compound of the formula I in which n is 0 or 2, $R^1$ and $R^2$ are hydrogen or methyl, $R^3$ and $R^4$ are methyl, phenyl, thienyl or phenyl which is substituted by methyl, methoxy or chlorine, $R^5$ and $R^6$ independently of one another are hydrogen or acetyl, X is one of the following groups:

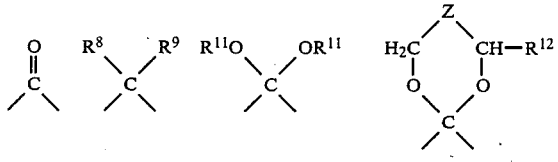

in which $R^8$ is hydrogen, methyl or —P(O)(OC$_1$–C$_4$alkyl)$_2$, $R^9$ is —OR$^{17}$, $R^{11}$ is $C_1$–$C_4$alkyl, $R^{12}$ is hydrogen, $C_1$–$C_4$alkyl or —CH$_2$OH, Z is a direct bond or a group —C(R$^{24}$)(R$^{25}$)—, $R^{17}$ is hydrogen, $C_2$–$C_{12}$alkanoyl, benzoyl or a group of the formula III in which m is 1 and $R^{21}$ is $C_2$–$C_8$alkylene, $R^{24}$ is a group —CH$_2$OH and $R^{25}$ is $C_1$–$C_4$alkyl.

Examples of compounds of the formula I are:
1. 4-oxo-2,2-dimethyl-thiane
2. 4-oxo-2,2,6,6-tetramethyl-thiane
3. 4-oxo-2,6-diphenyl-thiane
4. 4-oxo-2-phenyl-6,6-dimethyl-thiane
5. 4-oxo-2,6-bis-(4-chlorophenyl)-thiane
6. 4-oxo-2,6-bis-(4-methoxyphenyl)-thiane
7. 4-hydroxy-2,2,6,6-tetramethyl-thiane
8. 4-hydroxy-2,6-diphenyl-thiane
9. 4-hydroxy-2,6-bis-(4-chlorophenyl)-thiane
10. 4-hydroxy-2,6-bis-(4-methoxyphenyl)-thiane
11. 4-hydroxy-2,2,6,6-tetramethyl-thiane 1-oxide
12. 4-hydroxy-2,2,6,6-tetramethyl-thiane 1-dioxide
13. 4-hydroxy-2,6-diphenyl-thiane 1-oxide
14. 4-hydroxy-2,6-diphenyl-thiane 1-dioxide
15. 4-hydroxy-4-methyl-2,6-diphenyl-5-acetyl-thiane
16. 4-hydroxy-2,4,6-triphenyl-5-benzoyl-thiane
17. 4-hydroxy-2,6-dithienyl-thiane
18. 4-hydroxy-4-diethoxyphosphonyl-2,6-diphenyl-thiane
19. 4-lauroyl-thiane
20. 4-acetoxy-2,2,6,6-tetramethyl-thiane
21. 4-butyroyloxy-2,2,6,6-tetramethyl-thiane
22. 4-lauroyloxy-2,2,6,6-tetramethyl-thiane
23. 4-benzoyloxy-2,2,6,6-tetramethyl-thiane
24. 4-benzoyloxy-2,2,6,6-tetramethyl-thiane 1-oxide
25. 4-benzoyloxy-2,2,6,6-tetramethyl-thiane 1-dioxide
26. bis-(2,2,6,6-tetramethyl-4-thianyl) oxalate
27. bis-(2,2,6,6-tetramethyl-4-thianyl) adipate
28. 4-acetoxy-2,6-diphenyl-thiane
29. 4-lauroyloxy-2,6-diphenyl-thiane
30. 4-lauroyloxy-2,6-diphenyl-thiane 1-oxide
31. 4-benzoyloxy-2,6-bis-(4-chlorophenyl)-thiane
32. 4-lauryloxy-2,6-bis-(4-methoxyphenyl)-thiane
33. bis-(2,6-diphenyl-4-thianyl) malonate
34. bis-(2,6-diphenyl-4-thianyl) succinate
35. bis-(2,6-diphenyl-4-thianyl) adipate
36. bis-(2,6-diphenyl-4-thianyl) sebacate
37. 4,4-dimethoxy-2,6-diphenyl-thiane
38. 7,7,9,9-tetramethyl-1,4-dioxa-8-thia-spiro[4.5]-decane
39. 7,9-diphenyl-1,4-dioxa-8-thia-spiro[4.5]-decane
40. 7,9-diphenyl-1,4-dioxa-8-thia-spiro[4.5]-decane-8-oxide
41. 7,9-diphenyl-1,4-dioxa-8-thia-spiro[4.5]-decane-8-dioxide
42. 2-hydroxymethyl-7,9-diphenyl-1,4-dioxa-8-thia-spiro[4.5]-decane
43. 3-ethyl-3-hydroxymethyl-8,10-diphenyl-1,5-dioxa-9-thia-spiro[5.5]-undecane
44. 3-ethyl-3-hydroxymethyl-8,10-diphenyl-1,5-dioxa-9-thia-spiro[5.5]-undecane 9-oxide
45. 3-ethyl-3-hydroxymethyl-8,10-diphenyl-1,5-dioxa-9-thia-spiro[5.5]-undecane 9-dioxide
46. 3-ethyl-3-hydroxymethyl-8,10-bis-(4-chlorophenyl-1,5-dioxa-9-thia-spiro[5.5]-undecane
47. 2-acetoxymethyl-7,9-diphenyl-1,4-dioxa-8-thia-spiro[4.5]-decane
48. 2-butyroyloxymethyl-7,9-diphenyl-1,4-dioxa-8-thia-spiro[4.5]-decane
49. 2-benzoyloxymethyl-7,9-diphenyl-1,4-dioxa-8-thia-spiro[4.5]-decane
50. 3-ethyl-3-acetoxy-8,10-diphenyl-1,5-dioxa-9-thia-spiro[5.5]-undecane
51. 3-ethyl-3-lauroyloxymethyl-8,10-diphenyl-1,5-dioxa-9-thia-spiro[5.5]-undecane
52. 3-ethyl-3-benzoyloxymethyl-8,10-diphenyl-1,5-dioxa-9-thia-spiro[5.5]-undecane
53. 3-ethyl-3-caproyloxymethyl-8,10-diphenyl-1,5-dioxa-9-thia-spiro[5.5]-undecane
54. 1,3-diaza-8-thia-7,7,9,9-tetramethyl-2,4-dioxa-spiro[4.5]-decane
55. 3-octyl-1,3-diaza-8-thia-7,9-diphenyl-2,4-dioxa-spiro[4.5]-decane
56. 3-benzyl-1,3-diaza-8-thia-7,9-diphenyl-2,4-dioxa-spiro[4.5]-decane
57. 2,2,7,7,9,9-hexamethyl-8-thia-1-oxa-3-aza-4-oxo-spiro[4.5]-decane
58. 2,2-dimethyl-7,9-diphenyl-8-thia-1-oxa-3-aza-4-oxo-spiro[4.5]-decane
59. 4-acetamido-2,2,6,6-tetramethyl-thiane 60. 4-lauroyl-2,6-diphenyl-thiane and the compounds of the formulae
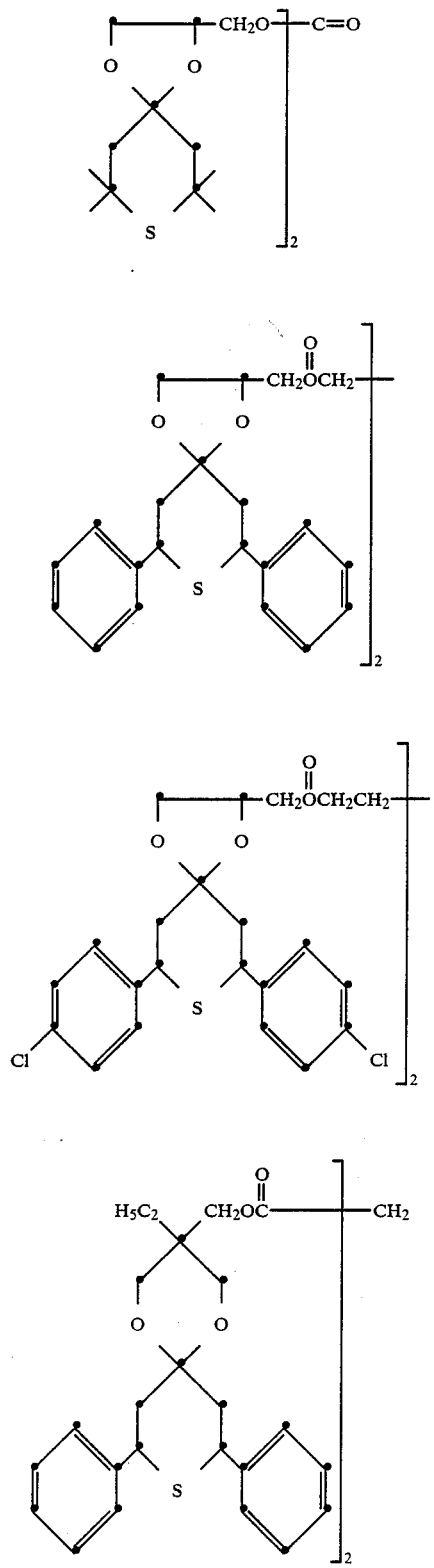
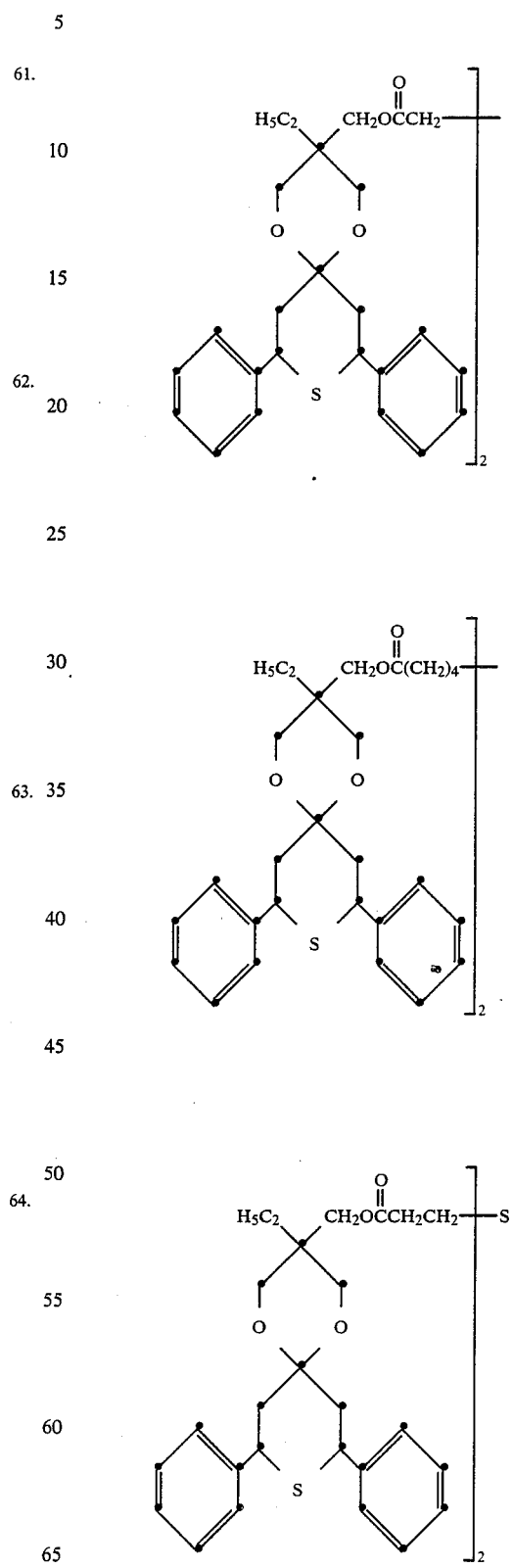

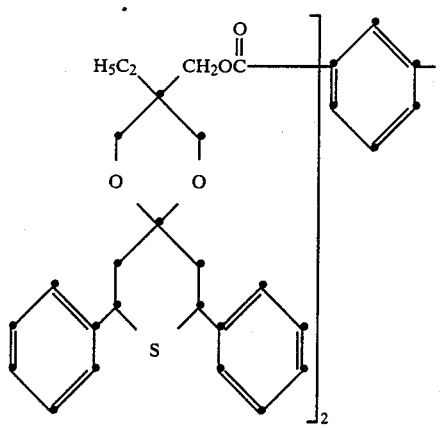

68.
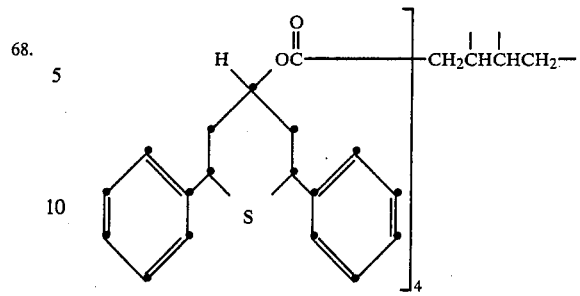

69.
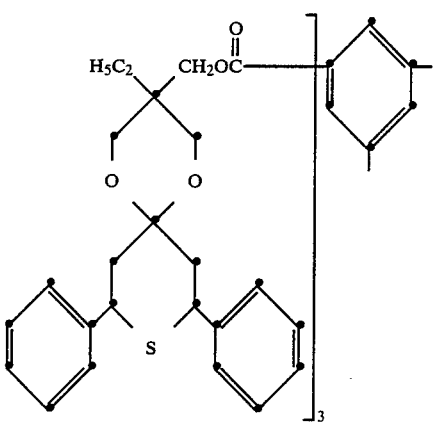

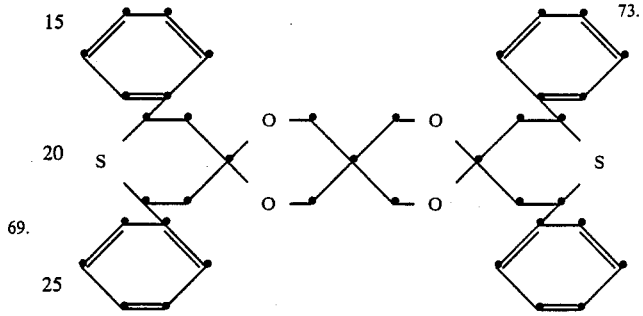

70.
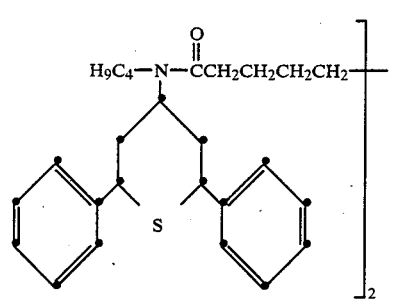

The stabilizers of the formula I are preferably used in combination with a phenolic antioxidant. Not only antioxidative stabilization but surprisingly also an increase in the photostabilizing effect is thereby effected. The invention thus also relates to a colour photography recording material containing (a) at least one tetrahydrothiopyran compound of the formula I and (b) at least one phenolic antioxidant.

Phenolic antioxidants are compounds with a sterically hindered phenolic group. Most of these compounds contain at least one group of the formula

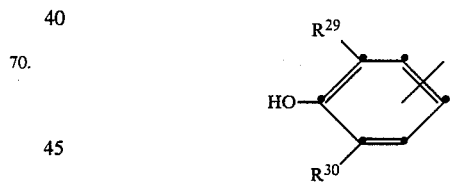

in which $R^{29}$ and $R^{30}$ independently of one another are $C_1$–$C_{12}$alkyl, cyclohexyl, phenyl or $C_7$–$C_9$phenylalkyl and $R^{30}$ can also be hydrogen.

Preferred components (b) are those antioxidants which contain at least one group of the formula 71.
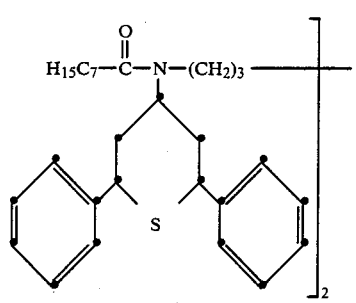

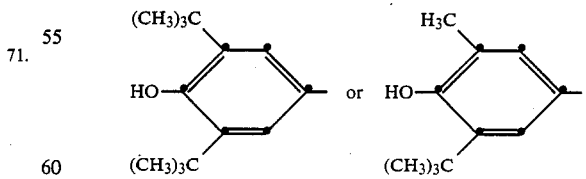

The phenolic antioxidant can also be an alkyl ether of a sterically hindered phenol.

Examples of such antioxidants which can be used as component (b) are the following compounds:

Alkylated monophenols, for example, 2,6-di-tert-butyl-4-methylphenol, 2-tert-butyl-4,6-dimethylphenol, 2,6-di-tert-butyl-4-ethylphenol, 2,6-di-tert-butyl-4-n- butylphenol, 2,6-di-tert-butyl-4-i-butylphenol, 2,6-dicyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol and 2,6-di-nonyl-4-methylphenol.

Alkylated hydroquinones, for example 2,6-di-tert-butyl-4-methoxyphenol, 2,5-di-tert-butyl-hydroquinone, 2,5-di-tert-amyl-hydroquinone and 2,6-di-phenyl-4-octadecyloxyphenol.

Hydroxylated thiodiphenyl ethers, for example 2,2'-thio-bis-(6-tert-butyl-4-methylphenol), 2,2'-thio-bis-(4-octylphenol), 4,4'-thio-bis-(6-tert-butyl-3-methylphenol) and 4,4'-thio-bis-(6-tertbutyl-2-methylphenol).

Alkylidene bisphenols, for example 2,2'-methylene-bis-(6-tert-butyl-4-ethylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butyl-phenol), 2,2'-ethylidene-bis-(6-tert-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethyleneglycol bis-[3,3-bis-(3'-tert-butyl-4'-hydroxyphenyl)-butyrate], bis-(3-tert-butyl-4-hydroxy-5-methylphenyl)-di-cyclopentadiene and bis-[2-(3'-tert-butyl-2'-hydroxy-5'-methyl-benzyl)-6-tert-butyl-4-methyl-phenyl] terephthalate.

Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzyl-mercaptoacetate, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, 3,5-di-tert-butyl-4-hydroxy-dioctadecyl 3,5-di-tert-butyl-4-hydroxybenzyl-phosphonate, the Ca salt of monoethyl 3,5-di-tert-butyl-4-hydroxybenzyl-phosphonate and 1,3,5-tris-(3,5-dicyclohexyl-4-hydroxybenzyl) isocyanurate.

Esters of β-(3,5-di-tert-butyl-4-hydroxyphenyl)-propionic acid with mono- or polyhydric alcohols, for example with methanol, octadecanol, 1,6-hexanediol, neopentylglycol, thiodiethylene glycol, diethylene glycol, triethylene glycol, pentaerythritol, tris-(hydroxyethyl) isocyanurate and N,N'-bis-(hydroxyethyl)-oxalic acid diamide.

Esters of β-(5-tert-butyl-4-hydroxy-3-methylphenyl)-propionic acid with mono- or polyhydric alcohols, for example with methanol, octadecanol, 1,6-hexanediol, neopentylglycol, thiodiethylene glycol, diethylene glycol, triethylene glycol, pentaerythritol, tris-(hydroxy)ethyl isocyanurate and N,N'-bis-(hydroxyethyl)-oxalic acid diamide.

Esters of β-(3,5-dicyclohexyl-4-hydroxyphenyl)-propionic acid with mono- or polyhydric alcohols, for example with methanol, octadecanol, 1,6-hexanediol, neopentylglycol, thiodiethylene glycol, diethylene glycol, triethylene glycol, pentaerythritol, tris-(hydroxy)ethyl isocyanurate and N,N'-bis-(hydroxyethyl)-oxalic acid diamide.

Esters of 3,5-di-tert-butyl-4-hydroxybenzoic acid with mono- or polyhydric alcohols or phenols, for example 2,4-di-tert-butylphenol or 2,4-di-tert-pentylphenol.

Amides of β-(3,5-di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

Further examples are the compounds of the following formulae:

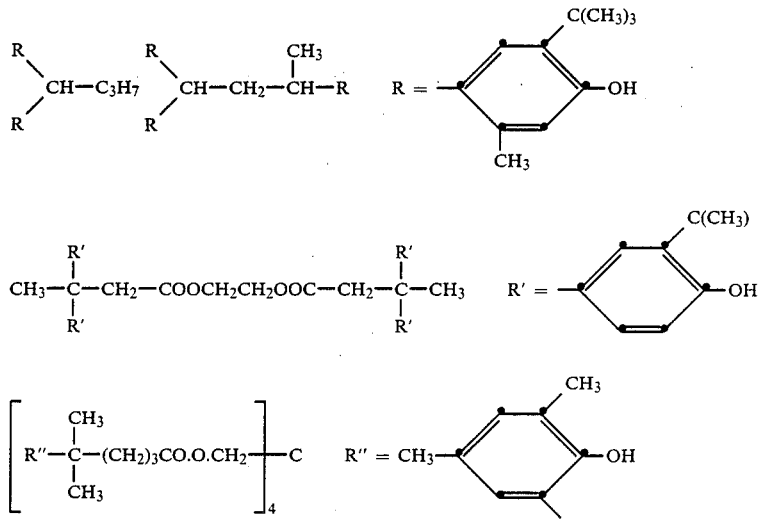

-continued
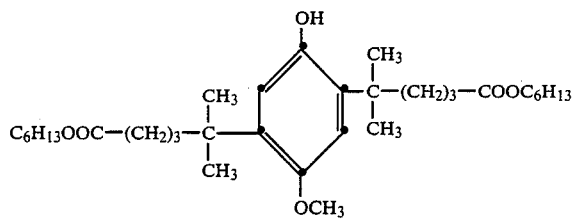
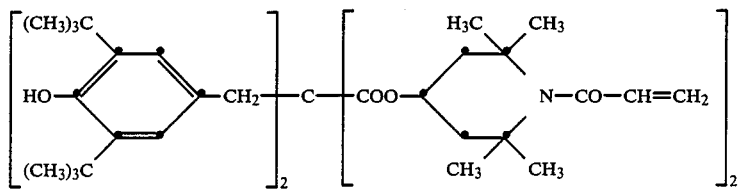
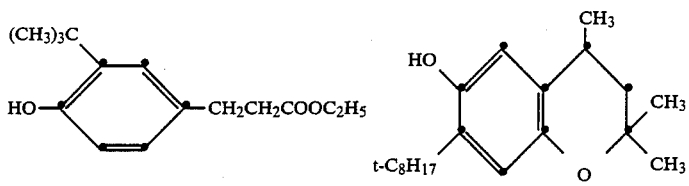
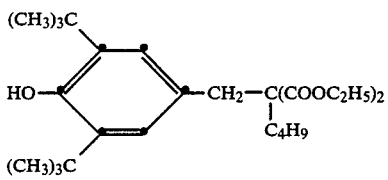
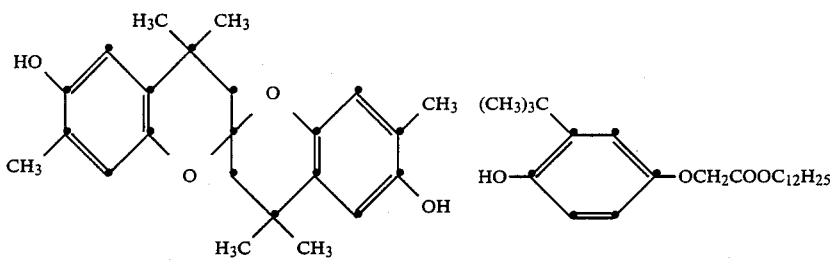
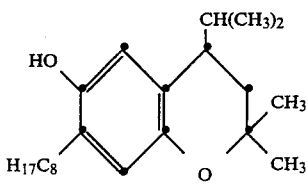
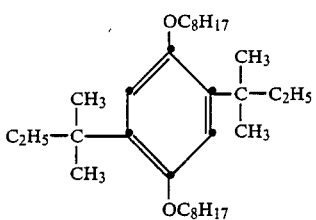

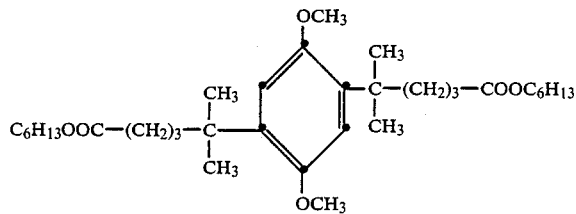

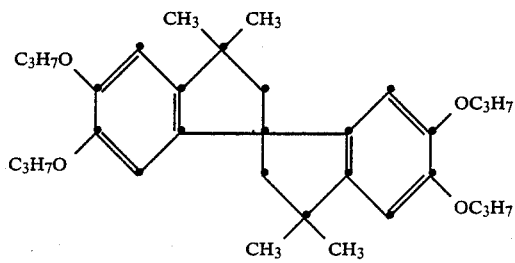

Instead of the free phenols, it is also possible to use masked phenols. Examples of these are esterified, sulfonylated, carbamoylated or silylated phenols. The free phenols are formed from these during the development.

The weight ratio of components (a) and (b) can be varied within a wide range. The ratio of (a):(b) is preferably 1:10 to 10:1, in particular 1:5 to 3:1.

If components (a) and (b) are water-soluble, they can be added as an aqueous solution to the photographic gelatin layer during its preparation. However, many of these compounds are only very slightly soluble in water and they are then dissolved in an organic solvent or solvent mixture and the solution is emulsified in a gelatin solution, which is then added to the photographic gelatin layer during its preparation. A mixture of a low-boiling and a high-boiling solvent is preferably used as the solvent and the low-boiling solvent is removed during the emulsification. Examples of low-boiling solvents which can be used are methyl acetate, ethyl acetate, carbon tetrachloride, methylene chloride, chloroform, methanol, ethanol, dioxane, acetone or benzene. Examples of high-boiling solvents are dimethylformamide, dimethyl sulfoxide, dialkyl phthalates or triaryl phosphates.

The stabilizer solution can be dispersed in the gelatin solution, for example, in a colloid mill or in a homogenizer or with the aid of ultrasound. Surface-active agents (emulsifiers) can also be added here. A fine dispersion is a prerequisite for homogeneous distribution of the stabilizers in the photographic layer.

The amount of stabilizer of the formula I added per layer is in general up to 1 g/m$^2$, preferably 10–300 mg/m$^2$. If a combination of (a) and (b) is used, the amount of (a+b) added is advantageously likewise up to 1 g/m$^2$ and preferably 10–300 mg/m$^2$.

The addition can be made to one or two or all three of the colour silver layers. Addition to the yellow layer is of particular importance. The layers contain the sensitized silver halide and the particular colour coupler. The layers can additionally contain further stabilizers and/or other additives.

The yellow couplers are preferably compounds of the formula IX

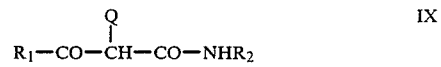

in which $R_1$ is alkyl or aryl, $R_2$ is aryl and Q is hydrogen or a group which can be split off by reaction with the oxidized developer.

A group of yellow couplers is formed by those compounds of the formula IX in which $R_1$ is tert-butyl and $R_2$ is a group of the formula

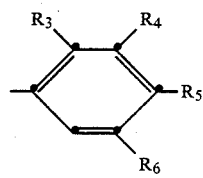

in which $R_3$ is hydrogen, halogen, alkyl or alkoxy and $R_4$, $R_5$ and $R_6$ are hydrogen, halogen, alkyl, alkenyl, alkoxy, aryl, carboxyl, alkoxycarbonyl, a carbamoyl group, a sulfone or sulfamoyl group or an alkylsulfonamido group, acylamino group, ureido group or amino group.

Preferably, $R_3$ is chlorine, $R_4$ and $R_5$ are hydrogen and $R_6$ is an acylamino group. These also include the compounds of the formula

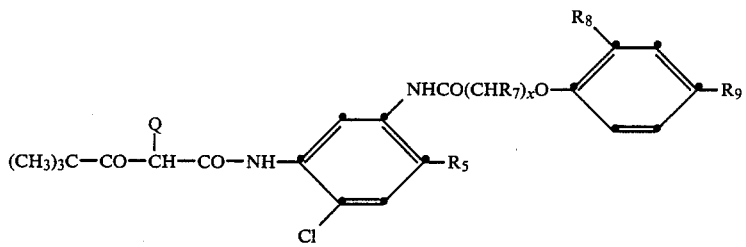

in which x is 0–4, $R_7$ is hydrogen or alkyl and $R_8$ and $R_9$ are alkyl.

Another group of yellow couplers corresponds to the formula X

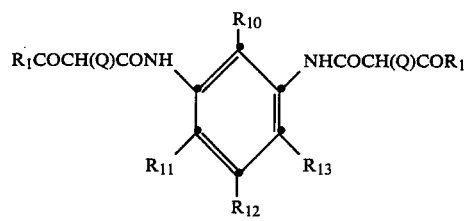 X in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, a carbamoyl group or a sulfone group, sulfamoyl group, sulfonamido group, acylamino group, ureido group or amino group and $R_1$ and Q have the above-mentioned meaning.

This includes compounds of the formula X in which $R_1$ is tert-butyl, $R_{10}$ is chlorine, $R_{11}$ and $R_{13}$ are hydrogen and $R_{12}$ is alkoxycarbonyl.

In the compounds of the formula IX and X, the leaving group Q can be hydrogen or halogen or is a heterocyclic group

in which $R_{14}$ is an organic divalent group which completes the ring to form a 4- to 7-membered ring, or Q is a group —$OR_{15}$ in which $R_{15}$ is alkyl, aryl, acyl or a heterocyclic radical.

Typical examples of customary yellow couplers are the compounds of the following formulae:

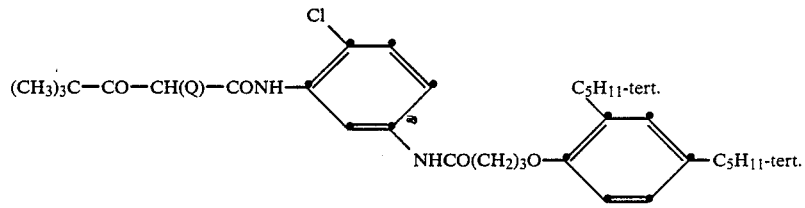

(a)

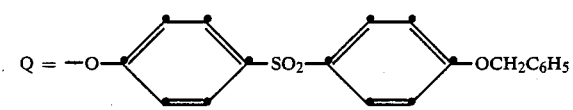

(b)

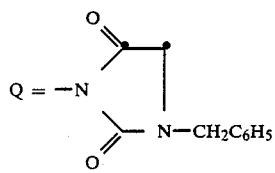

(c)

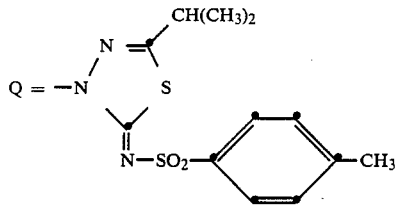

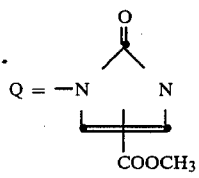
(d)

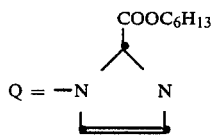
(e)

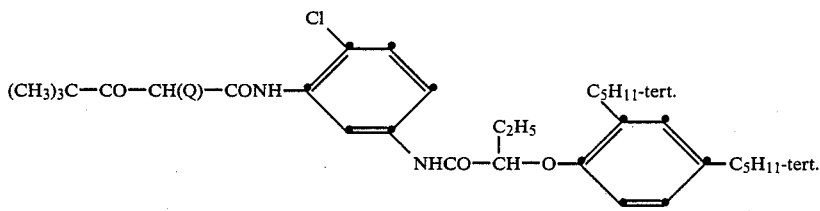
(f)

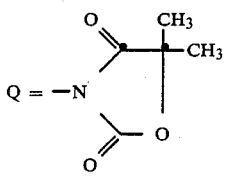
(g)

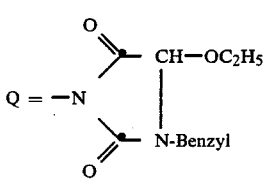

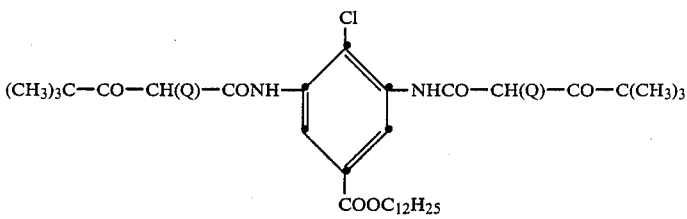

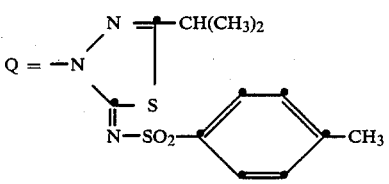
(h)

Further examples of yellow couplers are to be found in U.S. Pat. Nos. 2,407,210, 2,778,658, 2,875,057, 2,908,513, 2,908,573, 3,227,155, 3,227,550, 2,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, in DE-A 1,547,868, 2,057,941, 2,162,899, 2,163,813, 2,213,461, 2,219,917, 2,261,361, 2,261,362, 2,263,875, 2,329,587, 2,414,006 and 2,422,812 and in GB-A 1,425,020 and 1,077,874.

The yellow couplers are usually employed in an amount of 0.05-2 mol and preferably 0.1-1 mol per mol of silver halide.

Magenta couplers can be, for example, simple 1-aryl-5-pyrazolones or pyrazole derivatives fused with 5-membered hetero rings, for example imidazopyrazoles, pyrazolopyrazoles, pyrazolotriazoles or pyrazolotetrazoles.

One group of magenta couplers are 5-pyrazolones of the formula XI

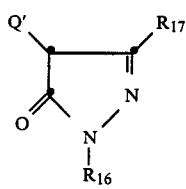

such as are described in British Patent Specification 2,003,473. In this formula, $R_{16}$ is hydrogen, alkyl, aryl, alkenyl or a heterocyclic group. $R_{17}$ is hydrogen, alkyl, aryl, a heterocyclic group or an ester group, alkoxy group, alkylthio group, carboxyl group, arylamino group, acylamino group, (thio)-urea group, (thio)-carbamoyl group, guanidino group or sulfonamido group.

Preferably, $R_{17}$ is a group

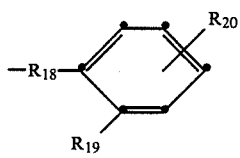

in which $R_{18}$ is imino, acylamino or ureido, $R_{19}$ is hydrogen, halogen, alkyl or alkoxy and $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Typical examples of this type of magenta couplers are compounds of the formula

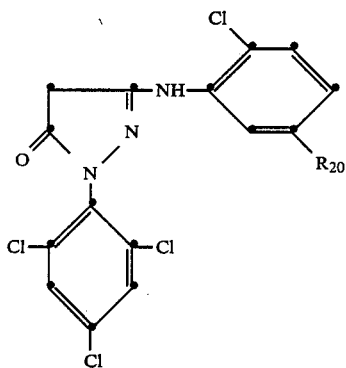

in which $R_{20}$ is as defined above.

Further examples of such tetraequivalent magenta couplers are to be found in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500.

If Q' in formula XI is not hydrogen but a group which is eliminated during the reaction with the oxidized developer, the compound is a diequivalent magenta coupler. Q' can in this case be, for example, halogen or a group bonded to the pyrazole ring via O, S or N. Such diequivalent couplers give a higher colour density and are more reactive towards the oxidized developer than the corresponding tetraequivalent magenta couplers. Q' is preferably an O-alkoxyarylthio group.

Examples of diequivalent magenta couplers are described in U.S. Pat. Nos. 3,006,579, 3,419,391, 3,311,476, 3,432,521, 3,214,437, 4,032,346, 3,701,783, 4,351,897 and 3,227,554, in EP-A-133,503, in DE-A-2,944,601 and in JP-A-78/34044, 74/53435, 74/53436, 75/53372 and 75/122935.

Two pyrazolone rings can be linked via a divalent Q' and so-called bis-couplers are then obtained. Such compounds are described, for example, in U.S. Pat. Nos. 2,632,702, 2,618,864, GB-A-968,461, GB-A-786,859 and JP-A-76/37646, 59/4086, 69/16110, 69/26589, 74/37854 and 74/29638.

As mentioned above, pyrazoles fused with 5-membered heterocyclic rings-so-called pyrazoloazoles - can also be used as magenta couplers. Their advantages over simple pyrazoles is that they have colours with a greater resistance to formalin and purer absorption spectra.

They can be represented by the general formula XII

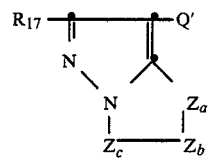

in which $Z_a$, $Z_b$ and $Z_c$ are the radicals to complete a 5-membered ring, which can contain up 4 nitrogen atoms. The compounds can accordingly be pyrazolo-imidazoles, pyrazolo-pyrazoles, pyrazolo-triazoles or pyrazolotetrazoles. $R_{17}$ and Q' have the same meanings as in formula XI.

Pyrazolo-tetrazoles are described in JP-A-85/33552; pyrazolo-pyrazoles are described in JP-A-85/43,695; pyrazolo-imidazoles are described in JP-A-85/35732, JP-A-86/18949 and U.S. Pat. No. 4,500,630; and pyrazolo-triazoles are described in JP-A-85/186,567, JP-A-86/47957, JP-A-85/215,687, JP-A-85/197,688, JP-A-85/172,982, EP-A-119,860, EP-A-173,256, EP-A-178,789, EP-A-178,788 and in Research Disclosure 84/24,624.

Further pyrazoloazole magenta couplers are described in: JP-A-86/28,947, JP-A-85/140,241, JP-A-85/262/160, JP-A-85/213,937, EP-A-177,765, EP-A-176,804, EP-A-170,164, EP-A-164,130, EP-A-178,794, DE-A-3,516,996, DE-A-3,508,766 and Research Disclosure 81/20919, 84/24531 and 85/25758.

Cyan couplers can be, for example, derivatives of phenol, of 1-naphthol or of pyrazoloquinazolone. Structures of the formula XIII

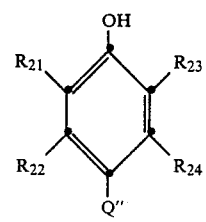

in which $R_{21}$, $R_{22}$, $R_{23}$ and $R_{24}$ are hydrogen, halogen, alkyl, carbamoyl, amido, sulfonamido, phosphoramido or ureido are preferred. $R_{21}$ is preferably H or Cl and $R_{22}$ is preferably an alkyl or amido group. $R_{23}$ is preferably an amido group and $R_{24}$ is preferably hydrogen. Q'' is hydrogen or a leaving group which is split off during the reaction with the oxidized developer. A detailed list of cyan couplers is to be found in U.S. Pat. No. 4,456,681.

Examples of customary cyan couplers are the following:

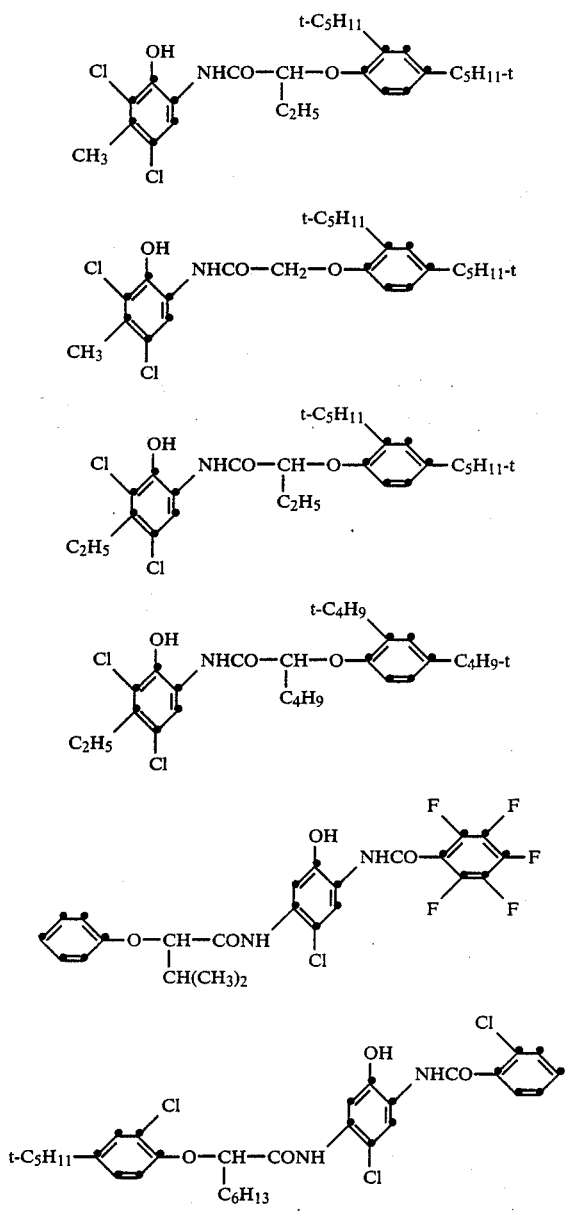

Further examples of cyan couplers are to be found in the following U.S. Pat. Nos.: 2,369,929, 2,423,730, 2,434,272, 2,474,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086 and 4,456,681.

The colour developers usually employed for colour photography materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-methanesulfonamidoethylaniline, 3-methyl-4-amino-N-ethyl-N-methoxyethyl-aniline, 3-α-methanesulfonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α-(α-methoxyethoxy)ethoxy]ethyl-3-methyl-4-aminoaniline and N-ethyl-N-α-(α-methoxyethoxy)ethyl-3-methyl-4-aminoaniline and the salts of such compounds, for example sulfates, hydro-chlorides or toluene-sulfonates.

The stabilizers according to the invention can be incorporated together with the colour coupler and if appropriate other additives into the colour photography material by predissolving them in high-boiling organic solvents. Solvents which have boiling points above 160° C. are preferably used. Typical examples of such solvents are the esters of phthalic acid, phosphoric acid, citric acid or benzoic acid or of fatty acids, and alkylamides and phenols.

A low-boiling solvent is usually also additionally used in order to facilitate the incorporation of the additives into the colour photography material. Examples of such solvents are esters, for example ethyl acetate, alcohols, for example butanol, ketones, for example methyl isobutyl ketone, chlorohydrocarbons, for example methylene chloride or amides, for example dimethylformamide. If the additives themselves are liquid, they can also be incorporated into the photographic material without the aid of solvents.

Further details on high-boiling solvents which can be used are to be found in the following patent specifications.

Phosphates: GB-A-791,219, BE-A-755,248 and JP-A-76/76739, 78/27449, 78/218,252, 78/97573, 79/148,113, 82/216,177, 82/93323 and 83/216,177.

Phthalates: GB-A-791,219 and JP-A-77/98050, 82/93322, 82/216,176, 82/218,251, 83/24321, 83/45699 and 84/79888.

Amides: GB-A-791,219, JP-A-76/105,043, 77/13600, 77/61089 and 84/189,251 and U.S. Pat. No. 928,741.

Phenols: GB-A-820,329, FR-A-1,200,657 and JP-A-69/69946, 70/3818, 75/123,026, 75/82078, 78/17914, 78/21166, 82/212,114 and 83/45699.

Other oxygen-containing compounds: U.S. Pat. Nos. 3,748,141 and 3,779,765, JP-A-73/75126, 74/101,114, 74/10115, 75/101,625, 76/76740 and 77/61089 and BE-A-826,039.

Other compounds: JP-A-72/115,369, 72/130,258, 73/127,521, 73/76592, 77/13193, 77/36294 and 79/95233 and Research Disclosure 82/21918.

The amount of high-boiling solvent is advantageously in the range from 0.1 to 300%, preferably 10 to 100%, based on the colour coupler.

The photographic layers can furthermore contain colour cast inhibitors. These prevent the formation of colour casts, such as are formed, for example, by reaction of the coupler with unintentionally oxidized developer or with by-products of the colour formation process. Such colour fog inhibitors are usually hydroquinone derivatives, but can also be derivatives of aminophenols, of gallic acid or of ascorbic acid. Typical examples of these are to be found in the following patent specifications: U.S. Pat. Nos. 2,360,290, 2,336,327, 2,403,721, 2,418,613, 2,675,314, 2,701,197, 2,704,713, 2,728,659, 2,732,300 and 2,735,365; EP-A-124,877; and JP-A-75/92988, 75/92989, 75/93928, 75/110,337 and 77/146,235.

The photographic layers can also contain so-called DIR couplers which give colourless compounds with the oxidized developer. They are added to improve the sharpness and grain structure of the colour pictures.

The photographic layers can also contain UV absorbers. These filter out the UV light and thus protect the dyes, the couplers or other components from photodegradation. Examples of such UV absorbers are 2-(2-hydroxyphenyl)-benzotriazoles, 2-hydroxybenzophenones, salicylic acid esters, acrylonitrile derivatives or thiazolines. Such UV absorbers are described in more detail, for example, in the following patent specifications: U.S. Pat. Nos. 3,314,794, 3,352,681, 3,705,805, 3,707,375, 4,045,229, 3,700,455, 3,533,794, 3,698,907, 3,705,805 and 3,738,837 and JP-A-71/2784. Preferred UV absorbers are the 2-(2-hydroxyphenol)-benzotriazoles.

The photographic layers can also contain phenolic compounds which act as light stabilizers for the colour picture and as a agents against colour fog. They can be contained in a photosensitive layer (colour layer) or in an intermediate layer, by themselves or together with other additives.

Such compounds are described in more detail in the following patent specifications: U.S. Pat. Nos. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146 and 4,559,297; GB-A-1,309,277, 1,547,302, 2,023,862, 2,135,788, 2,139,370 and 2,156,091; DE-A-2,301,060, 2,347,708, 2,526,468, 2,621,203 and 3,323,448; DD-A-200,691 and 214,468; EP-A-106,799, 113,124, 125,522, 159,912, 161,577, 164,030, 167,762 and 176,845; and JP-A-74/134,326, 76/127,730, 76/30462, 77/3822, 77/154,632, 78/10842, 79/48535, 79/70830, 79/73032, 79/147,038, 79/154,325, 79/155,836, 82/142,638, 83/224,353, 84/5246, 84/72443, 84/87456, 84/192,246, 84/192,247, 84/204,039, 84/204,040, 84/212,837, 84/220,733, 84/222,836, 84/228,249, 86/2540, 86,8843, 86/18835, 86/18836, 87/11456, 87/42245, 87/62157 and 86/6652 and in Research Disclosure 79/17804.

The photographic layers can also contain certain phosphorus-III compounds, in particular phosphites and phosphonites. These function as light stabilizers for the colour pictures and as dark storage stabilizers for magenta couplers. They are preferably added to the high-boiling solvents, together with the coupler. Such phosphorus-III compounds are described in more detail in the following patent specifications: U.S. Pat. Nos. 4,407,935, 4,436,811, EP-A-73/32728, JP-A-181,289, 76/1420 and JP-A-55/67741.

The photographic layers can also contain organometallic complexes which are light stabilizers for the colour pictures, in particular for the magenta dyes. Such compounds and the combination thereof with other additives are described in more detail in the following patent specifications: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165 and 4,590,153; JP-A-81/167,138, 81/168,652, 82/30834 and 82/161,744; EP-A-137,271, 161,577 and 185,506; and DE-A-2,853,865.

The photographic layers can also contain hydroquinone compounds. These act as light stabilizers for the colour couplers and for the colour pictures and as trapping agents of oxidized developer in intermediate layers. They are used in particular in the magenta layer. Such hydroquinone compounds and combinations thereof with other additives are described in more detail in the following patent specifications: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 2,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572 and 4,559,297; FR-A-885,982; GB-A-891;158, 1,156,167, 1,363,921, 2,022,274, 2,066,975, 2,071,348, 2,081,463, 2,117,526 and 2,156,091; DE-A-2,408,168, 2,726,283, 2,639,930, 2,901,520, 3,308,766, 3,320,483 and 3,323,699; DD-A-216,476, 214,468 and 214,469; EP-A-84290, 110,214, 115,305, 124,915, 124,877, 144,288, 147,747, 178,165 and 161,577; JP-A-75/33733, 75/21249, 77/128,130, 77/146,234, 79/70036, 79/133,131, 81/83742, 81/87040, 81/109,345, 83/134,628, 82/22237, 82/112,749, 83/17431, 83/21249, 84/75249, 84/149,348, 84/182,785, 84/180,557, 84/189,342, 84/228,249, 84/101,650, 79/24019, 79/25823, 86/48856, 86/48857, 86/27539, 86/6652, 86/72040, 87/11455 87/62157, and in Research Disclosure 79/17901, 79/17905, 79/18813, 83/22827 and 84/24014.

The photographic layers can also contain derivatives of hydroquinone ethers. These compounds act as light stabilizers and are particularly suitable for stabilizing magenta dyes. Such compounds and combinations thereof with other additives are described in more detail in the following patent specifications: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,314,011, 4,273,864, 4,264,720, 4,279,990, 4,332,886, 4,436,165, 4,360,589, 4,416,978, 4,385,111, 4,459,015 and 4,559,297; GB-A-1,347,556, 1,366,441, 1547,392, 1,557,237 and 2,135,788; DE-A-3,214,567; DD-214,469, EP-A-161,577, 167,762, 164,130 and 176,845; and JP-76/123,642, 77/35633, 77/147,433, 78/126, 78/10430, 78/53321, 79/24019, 79/25823, 79/48537, 79/45521, 79/56833, 79/70036, 79/70830, 79/73032, 79/95233, 79/145,530, 80/21004, 80/50244, 80/52057, 80/70840, 80/139,383, 81/30125, 81/151,936, 82/34552, 82/68833, 82/204,036, 82/204,037, 83/134,634, 83/207,039, 84/60434, 84/101,650, 84/87450, 84/149,348, 84/182,785, 86/72040, 87/11455, 87/62157, 87/63149, 86/2151, 86/6652 and 86/48855 and in Research Disclosure 78/17051.

Efforts to develop colour photography materials in an even shorter time and thereby to use chemicals which are easier to handle and pollute the environment less have led to considerable limitations in the choice of the components of the system. Thus, the silver halide emulsions used are those which are based largely or completely on silver chloride, which means that development time is shortened. It has furthermore been found that developer systems largely or completely lacking in benzyl alcohol can be used without the colour density thereby being reduced. This renders possible developer concentrates of fewer constituents, and with shorter mixing times and a lower toxicity of the spent developer. In order to achieve this aim of shortening the development time and reducing the benzyl alcohol, the following additives can be used:

(a) N-substituted hydroxylamines as antioxidants instead of the customary hydroxylamines, (b) development accelerators, for example 1-aryl-3-pyrazolones, hydrazine derivatives, quaternary ammonium and phosphonium compounds or polyoxyalkylene compounds, (c) triethanolamine as a tar-combating agent, (d) lithium salts, for example those of polystyrenesulfonates, and (e) aromatic polyhydroxy compounds, for example sodium 5,6-dihydroxy-1,2,4-benzenetrisulfonate.

The compounds of the formula I can also be used in such rapidly developing systems, such as in photographic layers based on silver chloride emulsions, and in systems which are developed completely or largely without benzyl alcohol.

Some of the compounds of the formula I are novel compounds. These include the compounds of the formula Ia

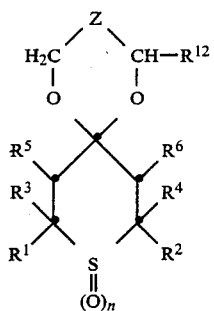

in which n, Z, $R^1$, $R^2$, $R^3$, $R^4$, $R^5$, $R^6$ and $R^{12}$ are as defined above for formula I. The invention likewise relates to these compounds. They can be prepared by ketalization of the corresponding 4-ketothianes of the formula XIV with diols of the formula XV:

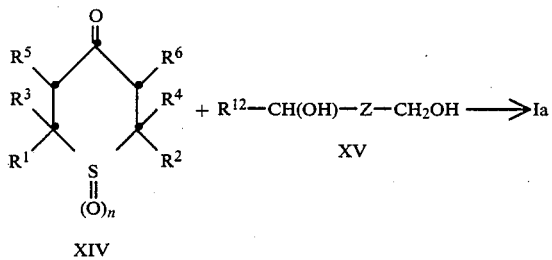

The reaction can be carried out by the customary methods of ketalization using acid catalysts. Sulfuric acid, p-toluenesulfonic acid or trifluoroacetic acid, for example, can be used as the catalyst. The reaction is preferably carried out in an inert solvent, for example in benzene, toluene, xylene or decalin. The water formed can be removed continuously from the reaction medium by distillation.

The following examples illustrate the invention in more detail. In these examples, parts and percentages are parts by weight as percentages by weight. The temperatures are stated in °C.

(A) PREPARATION EXAMPLES OF TETRAHYDROTHIOPYRANS (THIANES)

EXAMPLE 1

2.7 g of cis-2,6-diphenyl-4-hydroxythian (melting point 156°) are taken with 1.1 g of triethylamine in 50 ml of absolute toluene and the mixture is heated to 50°. A solution of 2.2 g of lauroyl chloride in 10 ml of absolute toluene are added dropwise in the course of about 10 minutes and the mixture is then stirred at 60° for 3 hours. It is allowed to cool to room temperature, the triethylamine hydrochloride which has precipitated is filtered off and the organic solution is washed three times with 50 ml of water each time and dried over sodium sulfate. The dry toluene solution is diluted with 50 ml of hexane, filtered over 40 g of silica gel and evaporated. Cis-2,6-diphenyl-4-lauroyloxythiane is obtained as a yellowish oil which is dried at 50° under 1.3 Pa.

EXAMPLE 2

3.3 g of cis-2,6-bis-(4-methoxyphenyl)-4-hydroxythiane are used instead of 2.7 g of cis-2,6-diphenyl-4-hydroxythiane and the procedure is otherwise as described in Example 1. Cis-2,6-bis-(4-methoxyphenyl)-4-lauroyloxythiane is obtained as a yellow oil.

EXAMPLE 3

67.1 g of 2,6-diphenyl-4-oxathiane are boiled with 35.3 g of trimethylolpropane and 2.0 g of p-toluenesulfonic acid monohydrate in 200 ml of toluene for 3 hours in a 350 ml flask with a KPG stirrer, water separator and thermometer, until no further water separates out. The contents of the flask are cooled to 35°-40° and washed twice with 50 ml of water each time. The toluene solution is evaporated to about half in vacuo and the crystal sludge formed is filtered off with suction and recrystallized from toluene. 3-Ethyl-3-hydroxymethyl-8,10-diphenyl-1,5-dioxa-9-thiaspiro[5.5]-undecane is obtained as colourless crystals of melting point 128°.

EXAMPLE 4

84.3 g of 2,6-bis-(4-chlorophenyl)-4-oxothiane are used instead of 67.1 g of 2,6-diphenyl-4-oxothiane and the procedure is otherwise as described in Example 3. 3-Ethyl-3-hydroxymethyl-8,10-bis-(4-chlorophenyl)-1,5-dioxa-9-thiaspiro[5.5]-undecane is obtained as colourless crystals of melting point 138°.

EXAMPLE 5

25 g of glycerol are used instead of 35.3 g of trimethylolpropane and the procedure is otherwise as described in Example 3. 2-Hydroxymethyl-7,9-diphenyl-1,4-dioxa-8-thiaspiro[4.5]-decane is obtained as colourless crystals of melting point 116°-118°.

EXAMPLE 6

13.4 g of 2,6-diphenyl-tetrahydrothiopyran-4-one are introduced into 25 ml of tert-butylamine. 15.2 g of diethyl phosphite are added dropwise at room temperature in the course of about 5 minutes. A weakly exothermic reaction can be detected, the solution becomes orange in colour and a precipitate slowly forms. The mixture is allowed to react completely at room temperature for 2 hours and the precipitate formed is filtered off and washed with 10 ml of tert-butylamine. The colourless residue is recrystallized from toluene. 2,6-

Diphenyl-4-hydroxy-4-diethoxyphosphonylthiane is obtained as colourless crystals of melting point 191°–192°.

EXAMPLE 7

3-Ethyl-3-hydroxymethyl-8,10-diphenyl-1,5-dioxa-9-thiaspiro[5.5]-undecane-9-dioxide is obtained as colourless crystals, which decompose at 257° C., analogously to Example 3 by reacting 75 g of 2,6-diphenyl-4-oxothiane-1-dioxide with 35.3 g of trimethylolpropane.

EXAMPLE 8

19.2 g of 3-ethyl-3-hydroxymethyl-8,10-diphenyl-1,5-dioxa-9-thiaspiro[5.5]-undecane and 6.8 g of methyl benzoate are dissolved in 100 ml of xylene. About 20 ml of xylene are distilled off under a weak stream of nitrogen. After cooling to 110°, 0.1 g of LiNH$_2$ are added and the mixture is heated at 135° for 8 hours, with stirring, the methanol formed being continuously distilled off together with a little xylene. After cooling to room temperature, 0.25 ml of glacial acetic acid and 3 g of bleaching earth are added. After stirring for 15 minutes, the mixture is filtered. The filtrate is filtered over 100 g of silica gel and evaporated in vacuo. The oily residue is dried at 70° in vacuo. 3-Ethyl-3-benzoyloxymethyl-8,10-diphenyl-1,5-dioxa-9-thiaspiro[5.5]-undecane is obtained as a pale yellowish resin.

EXAMPLE 9

6.5 g of methyl caproate are used instead of the methyl benzoate and the procedure is otherwise as described in Example 8. 3-Ethyl-3-carproyloxymethyl-8,10-diphenyl-1,5-dioxa-9-thiaspiro[5.5]-undecane is obtained as a yellowish resin.

EXAMPLE 10

10.7 g of methyl laurate are used instead of the methyl benzoate and the procedure is otherwise as described in Example 8. 3-Ethyl-3-lauroyloxymethyl-8,10-diphenyl-1,5-dioxa-9-thiaspiro[5.5]-undecane is obtained as a yellowish resin.

EXAMPLE 11

The compound of the formula

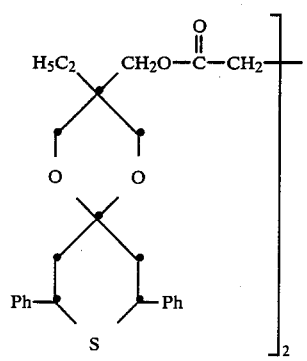

is obtained as a yellowish resin analogously to Example 8 from 23.3 g of 3-ethyl-3-hydroxymethyl-8,10-diphenyl-1,5-dioxa-9-thiaspiro[5.5]-undecane and 2.2 g of dimethyl succinate.

EXAMPLE 12

3.5 g of dimethyl sebacate are used instead of the dimethyl succinate and the procedure is otherwise as in Example 11. The compound of the formula

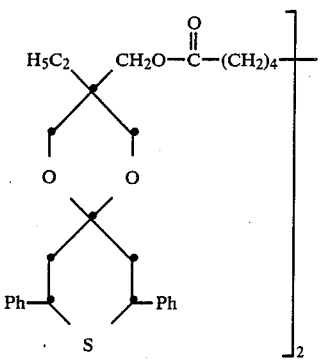

is obtained as a yellowish resin.

EXAMPLE 13

26.8 g of 2,6-diphenyl-4-oxothiane are reacted with 6.8 g of pentaerythritol analogously to Example 3 to give the compound of the formula

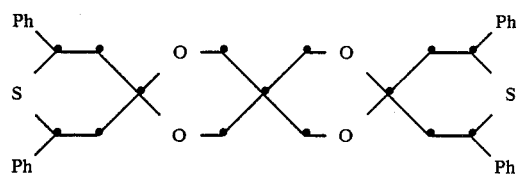

as colourless crystals which melt at 254°–256°.

EXAMPLE 14

7,9-Diphenyl-1,4-dioxa-8-thiaspiro[4.5]-decane is obtained as colourless crystals, which melt at 131°, analogously to Example 3 by reaction of 53.7 g of 2,6-diphenyl-4-oxothiane with 12.4 g of ethylene glycol.

EXAMPLE 15

23.4 g of 7,9-diphenyl-1,4-dioxa-8-thiaspiro[4.5]-decane are dissolved in 50 ml of methylene chloride and the solution is cooled to −10°. A solution of 16.0 g of m-chloroperbenzoic acid in 200 ml of methylene chloride is added dropwise in the course of about 7 hours, it being ensured that the temperature does not exceed −5°. The reaction mixture is then stirred at 0° for 16 hours and filtered and the residue is washed with 100 ml of methylene chloride. The combined methylene chloride solutions are washed three times with 150 ml of water each time, dried over sodium sulfate and evaporated. The colourless residue is stirred with 100 ml of 2N sodium hydroxide solution for 1 hour, filtered off, washed neutral, dried and crystallized from toluene. 7,9-Diphenyl-1,4-dioxa-8-thiaspiro[4.5]-decane 8-oxide is obtained as colourless crystals of melting point 230°–32°.

EXAMPLE 16

6.6 g of 7,9-diphenyl-1,4-dioxa-8-thiaspiro[4.5]-decane-8-oxide are dissolved in 50 ml of glacial acetic acid. 10 ml of 30% hydrogen peroxide are added dropwise to this solution at room temperature in the course of about 10 minutes and the mixture is then stirred at 50° for 2 hours. The reaction mixture is slowly diluted with 100 ml of water and the precipitate formed is filtered off with suction, washed with water and dried. Crystallization from toluene gives 7,9-diphenyl-1,4-dioxa-8-thiaspiro[4.5]-decane 8-dioxide as colourless crystals of melting point 264°.

(B) USE EXAMPLES
EXAMPLE I 0.087 g of the yellow coupler of the formula

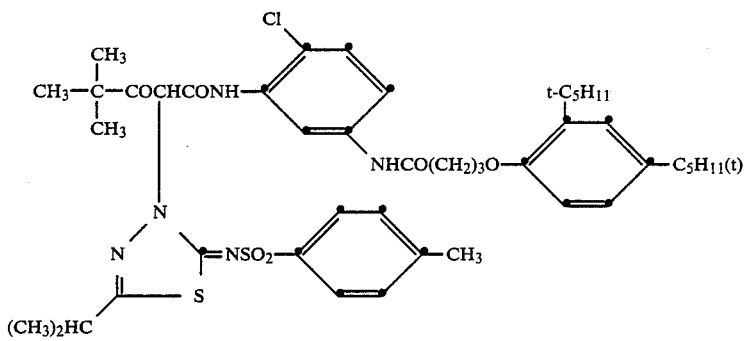

and the amounts of light stabilizer (mixture) shown in the table are dissolved in 2.0 ml of a mixture of tricresyl phosphate/ethyl acetate (1.5 g in 100 ml). 9 ml of a 2.3% gelatin solution which has been brought to a pH of 6.5 and contains 1.744 g/l of Nekal BX (Na diisobutylnaphthalenesulfonate) are added to 1 ml of this solution.

The mixture is then emulsified with ultra-sound at an output of 1000 watts for 3 minutes.

2 ml of a silver bromide emulsion with a silver content of 6.0 g per liter and 1 ml of a 0.7% aqueous solution of cyanuric acid dichloride, as a gelatin hardener, are added to 5 ml of the emulsion thus obtained and the mixture is poured onto substituted, plastic-coated white paper of 13×18 cm mounted on a glass plate.

After solidification, the system is dried in a drying cabinet with circulating air at room temperature. After 7 days, samples cut to 35×180 mm are exposed to 120 lux.s behind a step wedge and then developed in the Kodak Ektaprint 2 ® process.

The yellow wedges thus obtained are (a) irradiated in an Atlas Weather-Ometer with a 2500 W xenon lamp with a total of 30 kJ/cm², or (b) irradiated in an Atlas Weather-Ometer behind a UV filter (Kodak 2C) with a 2500 W xenon lamp with a total of 60 kJ/cm².

The percentage loss in colour density for an original density of 1.0 is shown in the following Tables 1–4.

The following stabilizers are used here:

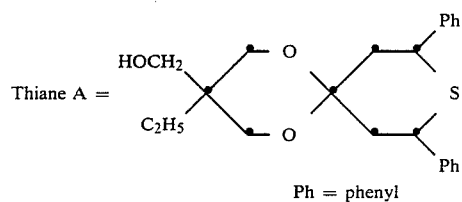

Ph = phenyl

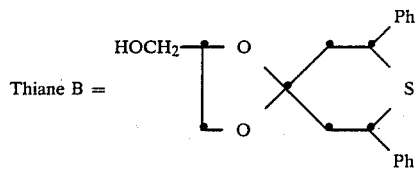

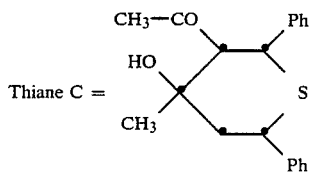

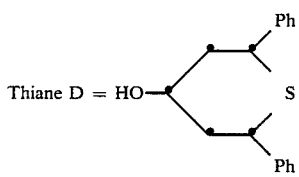

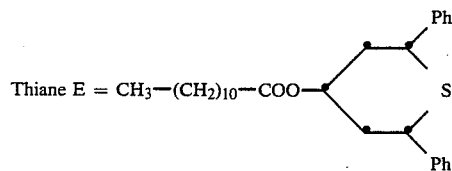
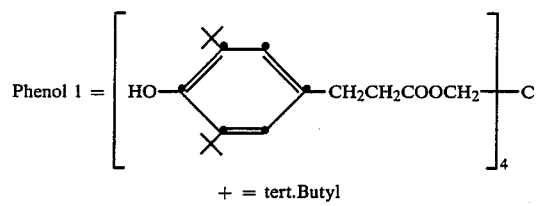
+ = tert.Butyl
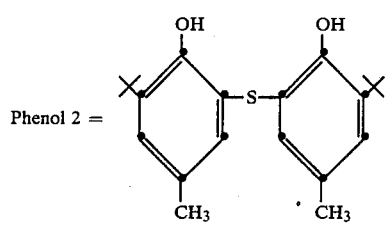
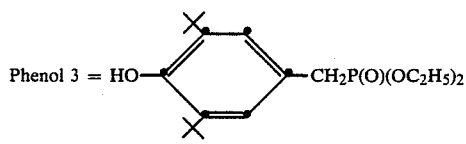
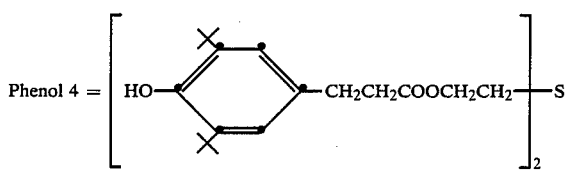
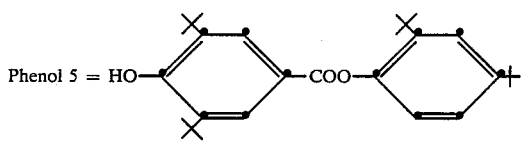
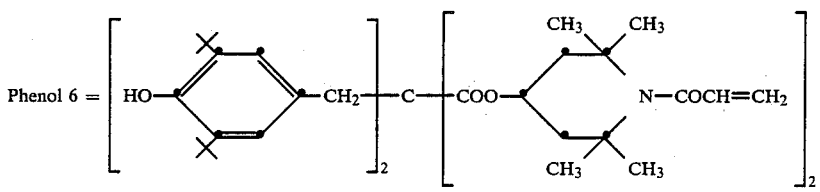
TABLE 1
| Light stabilizer | Amount (g) | Loss in density in % (reflectance) | |
|---|---|---|---|
| | | 30 kJ/cm² | 60 kJ/cm² (UV filter) |
| None | — | 61 | 22 |
| Thiane A | 0.026 | 58 | 14 |
| Thiane A + Phenol 1 | 0.013 0.013 | 42 | 11 |
| Thiane A | 0.026 | 58 | 14 |
| Thiane A + Phenol 2 | 0.013 0.013 | 50 | 14 |
| Thiane A | 0.026 | 58 | 14 |
| Thiane A + Phenol 3 | 0.013 0.013 | 41 | 13 |
TABLE 1-continued
| Light stabilizer | Amount (g) | Loss in density in % (reflectance) | |
|---|---|---|---|
| | | 30 kJ/cm² | 60 kJ/cm² (UV filter) |
| Thiane A | 0.026 | 58 | 14 |
| Thiane A + Phenol 4 | 0.013 0.013 | 32 | 10 |
| Thiane A | 0.026 | 58 | 14 |
| Thiane A + Phenol 6 | 0.009 0.013 | 41 | 11 |

TABLE 2

| Light stabilizer | Amount (g) | Loss in density in % (reflectance) 30 kJ/cm² | 60 kJ/cm² (UV filter) |
|---|---|---|---|
| None | — | 25 | |
| Thiane B | 0.026 | 19 | |
| Thiane B + Phenol 1 | 0.013 0.013 | 7 | |
| Thiane B | 0.026 | 17 | |
| Thiane B + Phenol 5 | 0.013 0.013 | 11 | |
| Thiane A | 0.026 | 11 | |
| Thiane A + Phenol 5 | 0.013 0.013 | 8 | |

TABLE 3

| Light stabilizer | Amount (g) | Loss in density in % (reflectance) 60 kJ/cm² (UV filter) |
|---|---|---|
| None | — | 32 |
| Thiane C | 0.026 | 25 |
| Thiane C + Phenol 1 | 0.013 0.013 | 11 |
| Thiane C | 0.026 | 25 |
| Thiane C + Phenol 2 | 0.013 0.013 | 21 |

TABLE 4

| Light stabilizer | Amount (g) | Loss in density in % (reflectance) 60 kJ/cm² (UV filter) |
|---|---|---|
| None | — | 25 |
| Thiane D | 0.026 | 19 |
| Thiane D + Phenol 5 | 0.013 0.013 | 11 |
| Thiane D | 0.026 | 19 |
| Thiane D + Phenol 1 | 0.013 0.013 | 9 |
| Thiane E | 0.026 | 15 |
| Thiane E + Phenol 5 | 0.013 0.013 | 11 |
| Thiane E | 0.026 | 15 |
| Thiane E + Phenol 1 | 0.013 0.013 | 9 |

EXAMPLE II 0.025 g of the cyan coupler of the formula

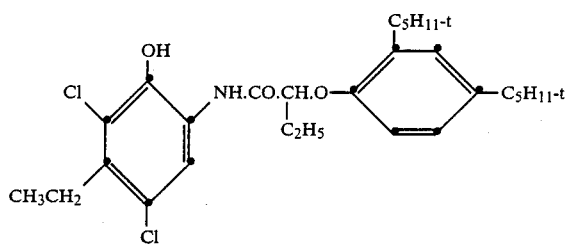

and 0.025 g of a light stabilizer shown in Table 5 are dissolved in 2 ml of a mixture of dibutyl phthalate/ethyl acetate (0.8 g/100 ml). 9 ml of a 2.3% aqueous gelatin solution which has been brought to a pH of 6.5 and contains 0.872 g/l of the wetting agent Nekal BX (Na diisobutylnaphthalene-sulphonate) are added to 1 ml of this solution. The mixture is then emulsified with ultra-sound for 3 minutes.

2 ml of a silver bromide emulsion with a silver content of 3 g per liter and 1 ml of a 0.7% aqueous solution of cyanuric acid dichloride, as a gelatin hardener, are added to 5 ml of the coupler emulsion thus obtained and the mixture is poured onto plastic-coated paper of 13×18 cm. After a hardening time of 7 days, the samples are exposed with 125 lux.s through a silver step wedge and are then processed in the Kodak Ektaprint 2 process.

The colour step wedges thus obtained are stored in a climate cabinet at 75° C. and 60% relative atmospheric humidity for 28 days.

The resulting percentage decreases in colour density for an original colour density of 1.0 are shown in the following table.

TABLE 5

| Stabilizer | Loss in density in % after 28 days at 75° C. |
|---|---|
| None | 12 |
| Thiane A | 6 |
| Thiane B | 6 |

EXAMPLE III 0.025 g of the cyan coupler of the formula

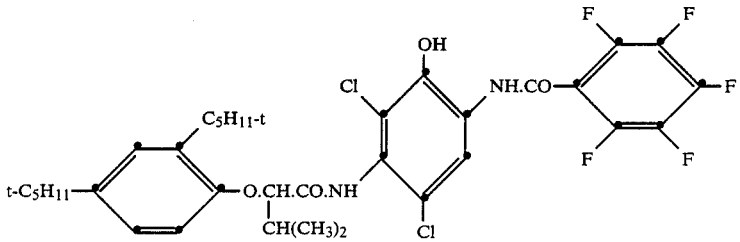

and the amount of one of the light stabilizers (or light stabilizer mixtures) shown in the following Tables 6 and 7 are dissolved in 2 ml of a mixture of dibutyl phthalate/ethyl acetate (0.8 g/100 ml). 9 ml of a 2.3% aqueous gelatin solution which has been brought to a pH of 6.5 and contains 0.872 g/l of the wetting agent Nekal BX (Na diisobutylnaphthalene-sulphonate) are added to 1 ml of this solution. The mixture is then emulsified with ultra-sound for 3 minutes.

2 ml of a silver bromide emulsion with a silver content of 3 g per liter and 1 ml of 0.7% aqueous solution of cyanuric acid dichloride, as a gelatin hardener, are added to 5 ml of the coupler emulsion thus obtained and the mixture is poured onto a plastic-coated paper of 13×18 cm. After a hardening time of 7 days, the samples are exposed with 125 lux.s through a silver step wedge and are then processed in the Kodak Ektaprint 2 process.

The colour step wedges thus obtained are irradiated in an Atlas Weather-Ometer behind a UV filter (Kodak 2C) with a 2500 W xenon lamp with a total of 60 kilojoules per cm².

The percentage decreases in colour density which thereby result for an original colour density of 1.0 are shown in the following Tables 6 and 7.

TABLE 6

| Stabilizer | Amount (g) | Loss in density in % (behind UV filter) 60 kJ/cm² |
|---|---|---|
| None | — | 35 |
| Thiane A | 0.026 | 24 |
| Thiane B | 0.026 | 24 |

TABLE 7

| Stabilizer | Amount (g) | Loss in density in % (behind UV filter) 60 kJ/cm² |
|---|---|---|
| None | — | 35 |
| Thiane A | 0.026 | 24 |
| Thiane B + phenol 5 | 0.013 0.013 | 18 |
| Thiane A | 0.026 | 24 |
| Thiane A + phenol 6 | 0.013 0.013 | 12 |

EXAMPLE IV 0.031 g of the magenta coupler of the formula

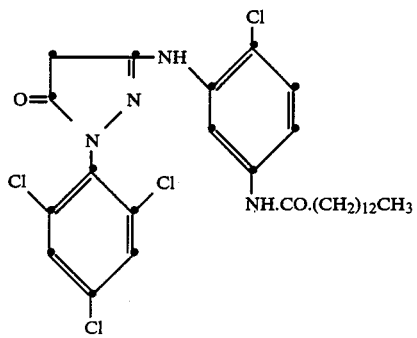

and the amount of one of the stabilizers (or stabilizer mixtures) shown in the following Table 8 are dissolved in 2 ml of a mixture of tricresyl phosphate/ethyl acetate (0.769 g/100 ml). 9.0 ml of a 2.3% aqueous gelatin solution which has been brought to a pH of 6.5 and contains 0.436 g/l of the wetting agent Nekal BX (Na diisobutyl-naphthalene-sulphonate) are added to 1 ml of this solution. The mixture is then emulsified with ultra-sound for 3 minutes.

2 ml of a silver bromide emulsion with a silver content of 6 g per liter and 1.0 ml of a 0.7% aqueous solution of cyanuric acid dichloride, as a gelatin hardener, are added to 5.0 ml of the coupler emulsion thus obtained and the mixture is poured onto a plastic-coated paper of 13×18 cm. After a hardening time of 7 days, the samples are exposed with 125 lux.s through a silver step wedge and are then processed in the Kodak Ektaprint 2 process.

The colour step wedges thus obtained are irradiated in an Atlas Weather-Ometer behind a UV filter (Kodak 2C) with a 3500 W xenon lamp with a total of 30 kilojoules per cm².

The increase in the yellow colour density in the non-exposed portion of the step wedge ($\Delta D_B$) is shown in the following Table 8.

TABLE 8

| Stabilizer | Amount (g) | $\Delta D_B$ |
|---|---|---|
| None | — | 16% |
| Thiane A | 0.011 | 6% |
| Thiane A + phenol 7 | 0.0055 0.0055 | 4% |
| Thiane F | 0.011 | 7% |
| Thiane F + phenol 7 | 0.0055 0.0055 | 5% |

Thiane F =

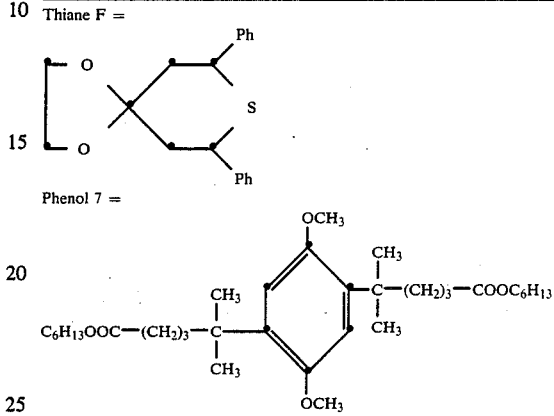

EXAMPLE V 0.027 g of the magenta coupler of the formula

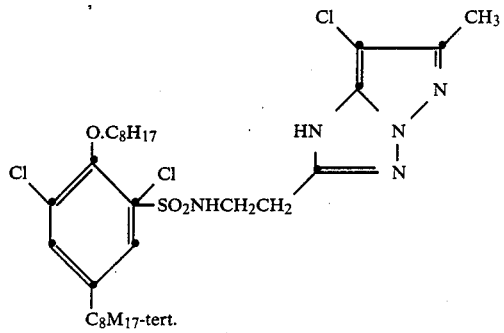

and the amount of one of the stabilizer mixtures shown in the following Table 9 are dissolved in 2 ml of a mixture of tricresyl phosphate/ethyl acetate (0.682 g/100 ml). 9.0 ml of a 2.3% aqueous gelatin solution which has been brought to a pH of 6.5 and contains 0.436/l of the wetting agent Nekal BX (Na diisobutylnaphthalene-sulphonate) are added to 1.0 ml of this solution. The mixture is then emulsified with ultra-sound for 3 minutes.

2 ml of a silver bromide emulsion with a silver content of 3 g per liter and 1.0 ml of a 0.7% aqueous solution of cyanuric acid dichloride, as a gelatin hardener, are added to 5.0 ml of the coupler emulsion thus obtained and the mixture is poured onto plastic-coated paper of 13×18 cm. After a hardening time of 7 days, the samples are exposed with 125 lux.s through a silver step wedge and are then processed in the Kodak Ektaprint 2 process.

The colour step wedges thus obtained are irradiated in an Atlas Weather-Ometer behind a UV filter (Kodak 2C) with a 2500 W xenon lamp with a total of 30 kilojoules per cm².

The percentage decrease in colour density is shown in the following Table 9.

TABLE 9

| Stabilizer | Amount (g) | Loss in density in % (reflectance) |
|---|---|---|
| None | — | 87 |
| Thiane A + Phenol 7 | 0,008 0,008 | 29 |
| Thiane A + Phenol 8 | 0,008 0,008 | 14 |
| Thiane A + Phenol 9 | 0,008 0,008 | 22 |
| Thiane A + Phenol 10 | 0,008 0,008 | 16 |
| Thiane E + Phenol 7 | 0,008 0,008 | 26 |
| Thiane E + Phenol 8 | 0,008 0,008 | 14 |
| Thiane E + Phenol 9 | 0,008 0,008 | 22 |
| Thiane E + Phenol 10 | 0,008 0,008 | 16 |
| Thiane F + Phenol 7 | 0,008 0,008 | 30 |
| Thiane F + Phenol 8 | 0,008 0,008 | 16 |
| Thiane F + Phenol 9 | 0,008 0,008 | 21 |
| Thiane F + Phenol 10 | 0,008 0,008 | 14 |

Phenol 8 =

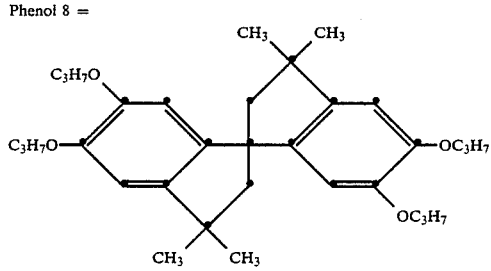

Phenol 9 =

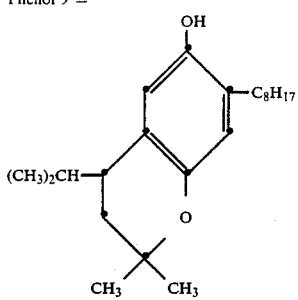

Phenol 10 =

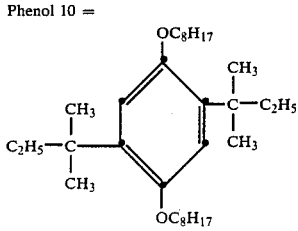

What is claimed is:

1. A colour photographic recording material comprising, on a support, at least one silver halide emulsion layer which contains a color coupler and at least one stablizer, said stabilizer being a compound of the formula I

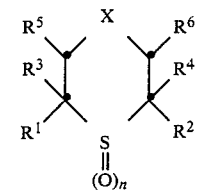

in which n is 0, 1 or 2, $R^1$ and $R^2$ independently of one another are hydrogen or methyl, $R^3$ and $R^4$ independently of one another are hydrogen, $C_1$-$C_4$alkyl, phenyl, theinyl or phenyl which is substituted by 1 or 2 $C_1$-$C_8$alkyl groups, cycohexyl, phenyl, $C_7$-$C_9$phenylalkyl, $C_1$-$C_{18}$alkoxy or halogen, $R^5$ and $R^6$ independently of one another are hydrogen, $C_1$-$C_4$alkyl, phenyl, —COO($C_1$-$C_{18}$alkyl), —CO—$CH_3$, —CO—phenyl, —CH(OR$^7$)—$CH_3$ or —CH(OR$^7$)—phenyl and $R^7$ is phydrogen, $C_1$-$C_{12}$alkyl, $C_2$-$C_{18}$alkanolyl or benzoyl, X is a divalent radical which completes the ring of the formula I to form a tetrahydrothiopyran ring and consists of one of the following groups:

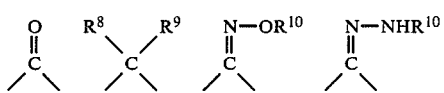

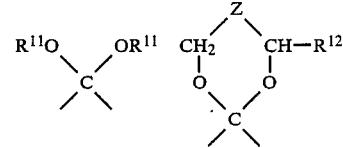

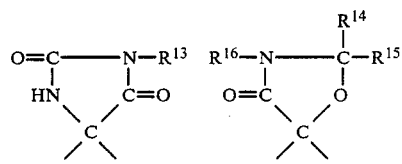

in which $R^8$ is hydrogen, methyl, phenyl, —CN, —CONH$_2$, —COO($C_1$-$C_4$alkyl) or —P(O)(O$C_1$-$C_4$alkyl)$_2$, $R^9$ is hydrogen, OR$^{17}$ or —N(R$^{18}$)(R$^{19}$), $R^{10}$ is hydrogen, $C_1$-$C_{18}$alkyl, $C_2$-$C_{18}$alkanoyl or benzoyl, $R^{11}$ is $C_1$-$C_{12}$alkyl, allyl or benzyl, $R^{12}$ is hydrogen, $C_1$-$C_4$alkyl or —CH$_2$OR$^{20}$, $R^{13}$ is hydrogen, $C_1$-$C_{18}$alkyl, $C_7$-$C_9$aralkyl, cyclohexyl or phenyl, $R^{14}$ and $R^{15}$ independently of one another are hydrogen, $C_1$-$C_{12}$alkyl or phenyl or $R^{14}$ and $R^{15}$ togther are $C_4$-$C_{11}$alkylene, $R^{16}$ is hydrogen, $C_1$-$C_{12}$alkyl, —COO($C_1$-$C_4$alkyl)-substituted $C_1$-$C_4$alkyl, allyl or benzyl, $R^{17}$ is hydrogen, $C_1$-$C_{12}$alkyl, allyl, benzyl, $C_2$-$C_{18}$alkanoyl, benzoyl, a group —CO—O—R$^{27}$ or —CO—NH—R$^{27}$ or a group of the formula II or III

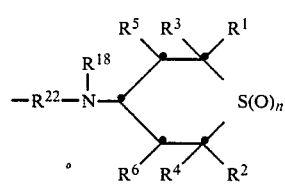

in which m is 1, 2 or 3, $R^{18}$ is hydrogen, $C_1$-$C_{12}$alkyl, $C_2$-$C_{18}$alkanoyl, benzoyl, $C_1$-$C_{12}$alkoxycarbonyl, phenoxycarbonyl or phenylaminocarbonyl, $R^{19}$ is hydrogen, $C_1$-$C_{12}$alkyl, cyclohexyl, benzyle, phenyl or a group of the formula IV

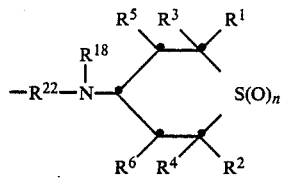

IV $R^{20}$ is hydrogen, $C_1$-$C_4$alkyl, $C_2$-$C_{18}$alkanoyl, benzoyl or a group of the formula V or VI

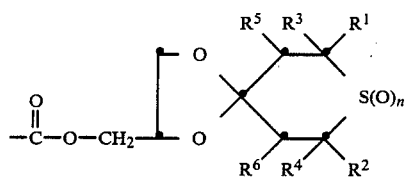

V

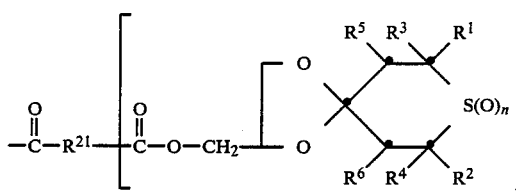

VI in which m is 1, 2, or 3, $R^{21}$, if m is 1, if m is 1, is a direct bond, $C_1$-$C_{12}$alkylene, $C_2$-$C_6$alkylene which is substituted by phenyl or benzyle or interrupted by —O— or —S—, vinylene, phenylene or a group —NH—$R^{2-}$ $_8$—NH—, and if m is 2, is $C_3$-$C_{12}$alkanetriyl or $C_6$-$C_{12}$arenetriyl, and m is 3, is $C_4$-$C_{12}$alkanetetrayl or $C_6$-$C_{12}$arenetetrayl, $R^{22}$ is $C_2$-$C_{12}$alkylene, $C_4$-$C_8$alkenylene, xylylene or a group —CO—$R^{23}$—CO—, in which $R^{23}$ is $C_1$-$C_{12}$alkylene which is substituted by phenyl or benzyl or interrupted by —O— or —S—, vinylene or phenylene, Z is a direct bond, a group

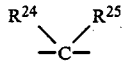

or a group of the formula

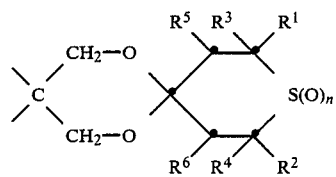

in which $R^{24}$ is hydrogen, $C_1$-$C_4$alkyl, —OH or —CH$_2$OR$^{26}$, $R^{25}$ is hydrogen or $C_1$-$C_4$alkyl and $R^{26}$ is hydrogen, $C_1$-$C_4$alkyl, $C_2$-$C_{18}$alkanoyl, benzoyl or a group of the formula VII or VIII

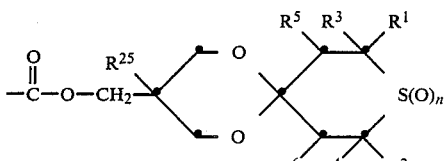

VII

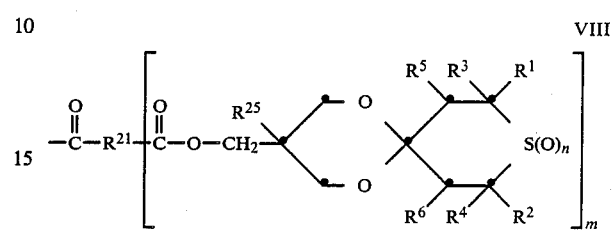

VIII in which m is 1, 2 or 3 $R^{27}$ is $C_1$-$C_{12}$alkyl or phenyl and $R^{28}$ is $C_1$-$C_{12}$alkylene, $C_6$-$C_{12}$cycloalkylene, phenylene, naphthylene or phenyl which is substituted by $C_1$-$C_4$aklyl, $C_1$-$C_4$alkoxy or halogen.

2. A colour photography recording material according to claim 1, containing at least one compound of the formula I in which n is 0 or 2, $R^1$ and $R^2$ are hydrogen or methyl, $R^{13}$ and $R^{14}$ are methyl, phenyl, thienyl or phenyl which is substituted by 1 or 2 $C_1$-$C_4$alkyl groups, by cyclohexyl, $C_1$-$C_4$alkoxy or chlorine, $R^5$ and $R^6$ independently of one another are hydrogen, methyl, acetyl or benzoyl, X is one of the following groups:

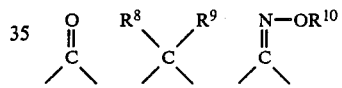

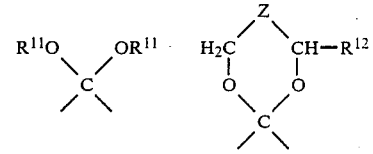

in which $R^8$ is hydrogen, mehtyl, phenyl or —P(O)(OC$_1$-$C_4$alkyl)$_2$, $R^9$ is hydrogen, —OR$^{17}$ or —NHR$^{18}$, $R^{10}$ is hydrogen or $C_2$-$C_{18}$alkanoyl, $R^{11}$ is $C_1$-$C_4$alkyl, $R^{12}$ is hydrogen, $C_1$-$C_4$alkyl or —CH$_2$OR$^{20}$, Z is a direct bond or a group —C(R$^{24}$)(R$^{25}$)—, $R^{17}$ is hydrogen, $C_2$-$C_{18}$alkanoyl, benzoyl or a group of the formula III in which m is 1 and $R^{21}$ is $C_1$-$C_{12}$alkylene, vinylene or phenylene, $R^{18}$ is $C_2$-$C_{12}$alkanoyl or benzoyl, $R^{20}$ is hydrogen, $C_2$-$C_{12}$alkanoyl, benzoyl or a group of the formula VI in which m is 1, $R^{24}$ is hydrogen, $C_1$-$C_4$alkyl or —CH$_2$OR$^{26}$, $R^{25}$ is hydrogen or $C_1$-$C_4$alkyl and $R^{26}$ is hydrogen, $C_2$-$C_{12}$alkanoyl, benzoyl or a group of the formula VIII in which m is 1.

3. A colour photography recording material according to claim 1, containing a compound of the formula 1 in which n is 0 or 2, $R^1$ and $R^2$ are hydrogen or methyl, $R^3$ and $R^4$ are methyl, phenyl, thienyl or phenyl which is substituted by methyl, methoxy or chlorine, $R^5$ and $R^6$ independently of one another are hydrogen or acetyl, X is one of the following groups:

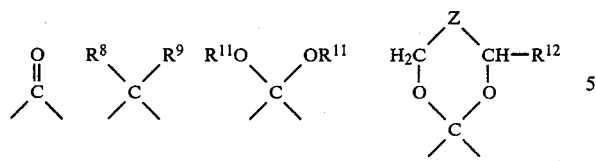

in which $R^8$ is hydrogen, methyl or $-P(O)(OC_1-C_4alkyl)_2$, $R^9$ is $-OR^{17}$, $R^{11}$ is $C_1-C_4alkyl$, $R^{12}$ is hydrogen, $C_1-C_4alkyl$ or $-CH_2OH$, Z is a direct bond or a group $-C(R^{24})(R^{25})-$, $R^{17}$ is hydrogen, $C_2-C_{12}alkanoyl$, benzoyl or a group of the formula III in which m is 1 and $R^{21}$ is $C_2-C_8alkylene$, $R^{24}$ is a group $-CH_2OH$ and $R^{25}$ is $C_1-C_4alkyl$.

4. A colour photography recording material according to claim 1, containing up to 1 g/m², preferably 10–300 mg/m², of a stablizer of the formula I.

5. A colour photography recording material according to claim 1, containing
(a) at least one tetrahydrothiopyran compound of the formula I and
(b) at least one phenolic antioxidant.

6. A colour photography recording material according to claim 5, in which component (b) is an antioxidant which contains at least one group of the formula

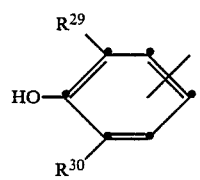

in which $R^{29}$ and $R^{30}$ independently of one another are $C_1-C_{12}alkyl$, cyclohexyl, phenyl or $C_7-C_9phenylalkyl$ and $R^{30}$ can also be hydrogen.

7. A colour photography recording matrial according to claim 1, in which component (b) is an antioxidant which contains at least one group of the formula

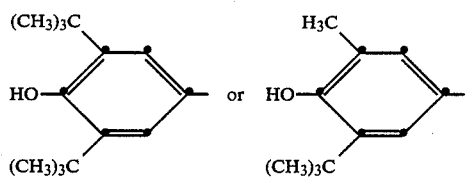

8. A colour photography recording material according to claim 5, in which component (b) is an alkyl ether of a sterically hindered phenol.

9. A colour photography recording material according to claim 5, containing up to 1 g/m² of the mixture of (a) and (b).

10. A colour photography recording material according to claim 5, containing 10–300 mg/m² of the mixture of (a) and (b).

11. A colour photographic recording material according to claim 1, wherein the stabilizer of the formula I is a compound of the formula

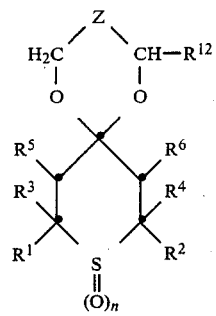

in which n is 0, 1 or 2, $R^1$ and $R^2$ independently of one another are hydrogen or methyl, $R^3$ and $R^4$ independently of one another are hydrogen, $C_1-C_4alkyl$, phenyl, theinyl or phenyl which is substituted by 1 or 2 $C_1-C_8alkyl$ groups, cyclohexyl, phenyl, $C_7-C_9phenylalkyl$, $C_1-C_{18}alkoxy$ or halogen, $R^5$ and $R^6$ independently of one another are hydrogen, $C_1-C_4alkyl$, phenyl, $-COO(C_1-C_{18}alkyl)$, $-CO-CH_3$, $-CO-phenyl$, $-CH(CR^7)-CH_3$ or $-CH(OR^7)-phenyl$ and $R^7$ is hydrogen, $C_1-C_{12}alkyl$, $C_2-C_{18}alkanoyl$ or benzoyl, $R^{12}$ is hydrogen, $C_1-C_4alkyl$ or $-CH_2-OR^{20}$, $R^{20}$ is hydrogen, $C_1-C_4alkyl$, $C_2-C_{18}alkanoyl$, benzoyl or a group of the formula V or VI

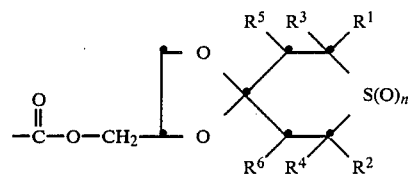

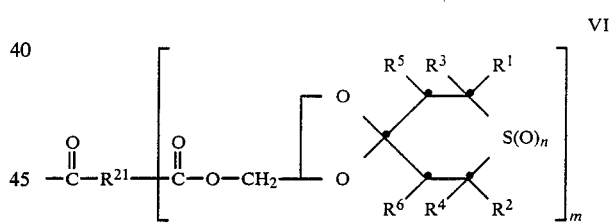

in which m is 1, 2 or 3, $R^{21}$, if m is 1, is a direct bond, $C_1-C_{12}alkylene$, $C_2-C_6alkylene$ which is substituted by phenyl or benzyl or interrupted by $-O-$ or $-S-$, vinylene, phenylene or a group $-NH-R^{28}-NH-$, and if m is 2, is $C_3-C_{12}alkanetriyl$ or $C_6-C_{12}arenetriyl$, and if m is 3, is $C_4-C_{12}alkanetetrayl$ or $C_6-C_{12}arenetetrayl$, and $R^{28}$ is $C_2-C_{12}alkylene$, $C_6-C_{12}cycloalkylene$, phenylene, naphthylene or phenylene which is substituted by $C_1-C_4alkyl$, $C_1-C_4alkoxy$ or halogen, Z is a direct bond or a group

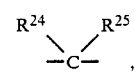

in which $R^{24}$ is hydrogen, $C_1-C_4alkyl$, $-OH$ or $-CH_2OR^{26}$, $R^{25}$ is hydrogen or $C_1-C_4alkyl$ and $R^{26}$ is hydrogen, $C_1-C_4alkyl$, $C_2-C_{18}alkanoyl$, benzoyl or a group of the formula VII or VIII

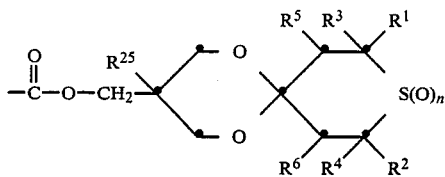
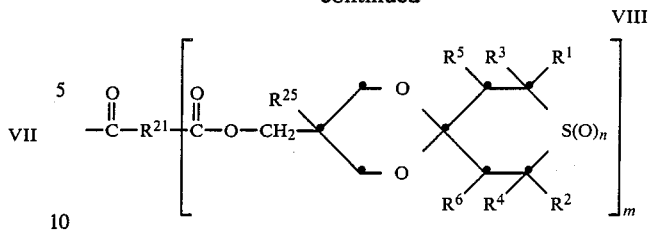
in which m is 1, 2 or 3.
12. A colour photographic recording material according to claim 11 wherein the stabilizer of formula Ia is present in combination with a phenolic antioxidant.
* * * * *